(12) United States Patent
Morissette et al.

(10) Patent No.: US 7,205,413 B2
(45) Date of Patent: Apr. 17, 2007

(54) SOLVATES AND POLYMORPHS OF RITONAVIR AND METHODS OF MAKING AND USING THE SAME

(75) Inventors: Sherry L. Morissette, Arlington, MA (US); Orn Almarsson, Shrewsbury, MA (US); Stephen Soukasene, Boston, MA (US)

(73) Assignee: TransForm Pharmaceuticals, Inc., Lexington, MA (US)

( * ) Notice: Subject to any disclaimer, the term of this patent is extended or adjusted under 35 U.S.C. 154(b) by 709 days.

(21) Appl. No.: 10/427,607

(22) Filed: May 1, 2003

(65) Prior Publication Data
US 2004/0024031 A1 Feb. 5, 2004

Related U.S. Application Data

(60) Provisional application No. 60/377,211, filed on May 3, 2002.

(51) Int. Cl.
*C07D 277/30* (2006.01)
*C07D 417/00* (2006.01)
*A01N 43/78* (2006.01)
*B65D 69/00* (2006.01)

(52) U.S. Cl. .................. 548/204; 546/269.7; 206/385; 206/885; 206/934; 206/570

(58) Field of Classification Search .................. 514/2; 424/1, 160.1; 548/146, 204; 546/269.7
See application file for complete search history.

(56) References Cited

U.S. PATENT DOCUMENTS

| | | | |
|---|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 5,059,595 A | 10/1991 | Le Grazie |
| 5,073,543 A | 12/1991 | Marshall et al. |
| 5,120,548 A | 6/1992 | McClelland et al. |
| 5,354,556 A | 10/1994 | Sparks et al. |
| 5,541,206 A | 7/1996 | Kempf et al. |
| 5,591,767 A | 1/1997 | Mohr et al. |
| 5,635,523 A | 6/1997 | Kempf et al. |
| 5,639,476 A | 6/1997 | Oshlack et al. |
| 5,674,533 A | 10/1997 | Santus et al. |
| 5,733,566 A | 3/1998 | Lewis |
| 5,846,987 A | 12/1998 | Kempf et al. |
| 5,886,036 A | 3/1999 | Kempf et al. |
| 6,037,157 A | 3/2000 | Norbeck et al. |
| 6,232,333 B1 | 5/2001 | Lipari et al. |
| 6,284,767 B1 | 9/2001 | Sham et al. |
| 6,977,723 B2 | 12/2005 | Lemmo et al. |
| 7,061,605 B2 | 6/2006 | Lemmo et al. |

FOREIGN PATENT DOCUMENTS

| | | |
|---|---|---|
| WO | WO00/04016 | 1/2000 |
| WO | WO 00/04016 A2 * | 1/2000 |
| WO | WO01/51919 | 7/2001 |

OTHER PUBLICATIONS

Bauer, J., et al., Pharm. Res., 18(6):859-866 (2001).
Chemburkar, S., et al., Organic Process Research and Development, 4:413-417 (2000).
Kumar, G.N., et al., Drug Metabolism and Disposition, 27(8):902-908 (1999).
Law, D., et al., Journal of Pharmaceutical Sciences, 90(8): 1015-1025 (2001).
Press Release, "Abbott Announces Difficulty Manufacturing Norvir® (ritonavir) Capsules", Abbott Park, Illinois, Jul. 27, 1998.
Press Release, "Abbott Laboratories Submits New Drug Application to U.S. Food and Drug Administration for Reformulated Norvir® Capsules", Abbott Park, Illinois, Mar. 31, 1999.
Press Release, "Abbott Laboratories Receives U.S. FDA Approval for Reformulated Norvir® (ritonavir) Capsule", Abbott Park, Illinois, Jun. 30, 1999.
Press Release, "Abbott Laboratories Receives European Commission Marketing Authorization for Reformulated Norvir® (ritonavir) Capsules", Abbott Park, Illinois, Dec. 1, 1999.
Press Release, "Studies of Norvir® (ritonavir) Combined with Other Protease Inhibitors Show Promise in HIV", Abbott Park, Illinois, Feb. 3, 2000.

* cited by examiner

*Primary Examiner*—Sreeni Padmanabhan
*Assistant Examiner*—Kendra D. Carter
(74) *Attorney, Agent, or Firm*—Paul Burgess

(57) ABSTRACT

Novel solvates and crystal polymorphs of Ritonavir are disclosed, as well as methods of making them. Specific solvates of the compound include a formamide solvate and a partially desolvated solvate. Also disclosed are methods of making previously known forms of Ritonavir. Methods of using the novel forms of Ritonavir for the treatment of diseases, such as HIV-infection, are disclosed, as are pharmaceutical compositions and unit dosage forms comprising the novel forms of Ritonavir.

6 Claims, 20 Drawing Sheets

| 2-Theta | d(A) | Height | Area | 2-Theta | d(A) | Height | Area |
|---|---|---|---|---|---|---|---|
| 3.33 | 26.5109 | 594 | 8690 | 21.55 | 4.1202 | 922 | 19193 |
| 6.79 | 13.0077 | 545 | 7904 | 22.492 | 3.9499 | 55 | 1155 |
| 8.369 | 10.5561 | 467 | 6675 | 23.55 | 3.7747 | 220 | 3603 |
| 10.588 | 8.3485 | 63 | 845 | 24.449 | 3.6379 | 107 | 1566 |
| 13.53 | 6.5392 | 111 | 2306 | 25.21 | 3.5298 | 85 | 1533 |
| 14.67 | 6.0334 | 155 | 2950 | 26.109 | 3.4103 | 97 | 1321 |
| 16.39 | 5.4041 | 232 | 9380 | 26.551 | 3.3545 | 89 | 5016 |
| 17.129 | 5.1724 | 365 | 11135 | 27.07 | 3.2914 | 92 | 4499 |
| 18.11 | 4.8944 | 530 | 7960 | 27.51 | 3.2397 | 67 | 997 |
| 18.71 | 4.7388 | 228 | 4203 | 28.609 | 3.1176 | 68 | 1487 |
| 19.55 | 4.5371 | 235 | 3451 | 29.13 | 3.0631 | 64 | 4162 |
| 19.93 | 4.4515 | 271 | 8977 | 34.61 | 2.5896 | 71 | 1632 |
| 20.31 | 4.3689 | 296 | 8186 | | | | |

| 2-Theta | d(A) | Height | Area | 2-Theta | d(A) | Height | Area |
|---|---|---|---|---|---|---|---|
| 6.392 | 13.8155 | 170 | 3686 | 23.492 | 3.7839 | 272 | 3860 |
| 8.624 | 10.245 | 1507 | 24046 | 24.111 | 3.6881 | 349 | 9692 |
| 9.516 | 9.2867 | 833 | 22726 | 24.781 | 3.5899 | 267 | 2832 |
| 9.815 | 9.0044 | 1169 | 20078 | 25.365 | 3.5086 | 774 | 10434 |
| 10.93 | 8.0881 | 732 | 9645 | 26.178 | 3.4015 | 466 | 15333 |
| 13.269 | 6.6671 | 209 | 6907 | 26.899 | 3.3118 | 142 | 1712 |
| 13.728 | 6.4453 | 876 | 19160 | 27.49 | 3.242 | 92 | 1028 |
| 14.857 | 5.958 | 140 | 1585 | 28.64 | 3.1143 | 590 | 11716 |
| 15.67 | 5.6506 | 224 | 2922 | 29.922 | 2.9838 | 395 | 10098 |
| 16.078 | 5.5082 | 969 | 21277 | 31.684 | 2.8218 | 386 | 10385 |
| 16.634 | 5.3254 | 774 | 14965 | 32.07 | 2.7887 | 201 | 5685 |
| 17.35 | 5.1072 | 1234 | 19446 | 33.21 | 2.6955 | 126 | 1921 |
| 17.75 | 4.9929 | 2591 | 37852 | 33.688 | 2.6583 | 140 | 4322 |
| 18.351 | 4.8307 | 2360 | 33079 | 35.123 | 2.5529 | 177 | 4362 |
| 18.909 | 4.6895 | 858 | 10075 | 36.278 | 2.4743 | 198 | 3978 |
| 19.51 | 4.5463 | 587 | 22292 | 37.334 | 2.4067 | 97 | 1344 |
| 20.019 | 4.4318 | 1365 | 50468 | 38.035 | 2.3639 | 57 | 1041 |
| 20.6 | 4.3081 | 1338 | 19974 | 38.429 | 2.3406 | 80 | 2016 |
| 21.652 | 4.1011 | 1772 | 35142 | 39.087 | 2.3027 | 96 | 987 |
| 22.164 | 4.0074 | 605 | 13157 | 40.596 | 2.2205 | 129 | 2025 |
| 22.719 | 3.9108 | 346 | 5573 | | | | |

| 2-Theta | d(A) | Height | Area | 2-Theta | d(A) | Height | Area |
|---|---|---|---|---|---|---|---|
| 3.069 | 28.7651 | 3603 | 49123 | 19.749 | 4.4918 | 523 | 10254 |
| 6.122 | 14.4255 | 151 | 1440 | 20.511 | 4.3267 | 1113 | 15529 |
| 6.818 | 12.9534 | 848 | 10708 | 20.975 | 4.2318 | 284 | 3815 |
| 7.652 | 11.5438 | 540 | 7149 | 21.758 | 4.0813 | 1175 | 27795 |
| 8.311 | 10.6304 | 401 | 5268 | 22.23 | 3.9958 | 394 | 13208 |
| 9.22 | 9.5846 | 208 | 2528 | 22.622 | 3.9275 | 187 | 2064 |
| 10.503 | 8.4157 | 386 | 6309 | 23.136 | 3.8413 | 85 | 211 |
| 12.104 | 7.3065 | 480 | 6638 | 23.752 | 3.743 | 783 | 15470 |
| 13.073 | 6.7665 | 487 | 7142 | 24.263 | 3.6654 | 129 | 1323 |
| 13.855 | 6.3866 | 50 | 458 | 25.081 | 3.5477 | 190 | 4609 |
| 14.902 | 5.9401 | 576 | 8319 | 26.399 | 3.3735 | 321 | 14134 |
| 15.828 | 5.5945 | 55 | 455 | 26.954 | 3.3052 | 236 | 5908 |
| 16.638 | 5.324 | 77 | 931 | 27.449 | 3.2467 | 159 | 2677 |
| 17.393 | 5.0946 | 268 | 4298 | 27.854 | 3.2004 | 47 | 459 |
| 17.924 | 4.9448 | 491 | 6857 | 28.471 | 3.1324 | 52 | 648 |
| 18.536 | 4.7828 | 760 | 13703 | 29.045 | 3.0718 | 218 | 4694 |
| 18.87 | 4.699 | 458 | 11589 | 29.712 | 3.0044 | 159 | 3137 |
| 19.371 | 4.5787 | 806 | 12423 | 30.551 | 2.9238 | 75 | 712 |

| 2-Theta | d(A) | Height | Area | 2-Theta | d(A) | Height | Area |
|---|---|---|---|---|---|---|---|
| 3.068 | 28.7735 | 10528 | 145664 | 19.741 | 4.4936 | 1923 | 34304 |
| 6.133 | 14.3989 | 405 | 4026 | 20.505 | 4.3278 | 3422 | 47146 |
| 6.825 | 12.9401 | 2766 | 34393 | 20.983 | 4.2302 | 1113 | 12598 |
| 7.65 | 11.5476 | 1460 | 17574 | 21.764 | 4.0804 | 4278 | 88481 |
| 8.302 | 10.6415 | 1324 | 16972 | 22.174 | 4.0058 | 1513 | 33840 |
| 9.23 | 9.5734 | 583 | 7611 | 22.632 | 3.9256 | 746 | 8396 |
| 10.501 | 8.4173 | 1149 | 14604 | 23.1 | 3.8472 | 116 | 369 |
| 12.105 | 7.3058 | 1335 | 19904 | 23.759 | 3.742 | 2813 | 48934 |
| 13.076 | 6.7653 | 1572 | 25326 | 24.321 | 3.6568 | 308 | 1700 |
| 13.792 | 6.4155 | 153 | 1417 | 25.139 | 3.5396 | 579 | 11745 |
| 14.909 | 5.9374 | 1857 | 25507 | 26.378 | 3.3761 | 1240 | 53248 |
| 15.833 | 5.5927 | 171 | 2208 | 26.913 | 3.3102 | 810 | 22510 |
| 16.651 | 5.3198 | 217 | 2484 | 27.441 | 3.2477 | 657 | 9732 |
| 17.39 | 5.0955 | 1270 | 17740 | 27.889 | 3.1966 | 182 | 485 |
| 17.926 | 4.9444 | 2299 | 29276 | 28.455 | 3.1342 | 241 | 1564 |
| 18.536 | 4.7829 | 2869 | 41642 | 29.041 | 3.0723 | 730 | 12819 |
| 18.894 | 4.6931 | 2009 | 34343 | 29.716 | 3.004 | 590 | 12684 |
| 19.353 | 4.5828 | 3514 | 47522 | 30.548 | 2.924 | 208 | 1690 |

| 2-Theta | d(A) | Height | Area | 2-Theta | d(A) | Height | Area |
|---|---|---|---|---|---|---|---|
| 3.37 | 26.2 | 1085 | 15753 | 24.526 | 3.6266 | 537 | 12674 |
| 6.39 | 13.8209 | 955 | 12971 | 25.066 | 3.5498 | 140 | 1410 |
| 6.79 | 13.0079 | 248 | 4281 | 25.57 | 3.4809 | 148 | 4027 |
| 7.609 | 11.6097 | 122 | 823 | 25.856 | 3.4431 | 182 | 7143 |
| 9.912 | 8.9168 | 2311 | 33741 | 26.447 | 3.3674 | 961 | 17072 |
| 11.25 | 7.8587 | 56 | 275 | 27.478 | 3.2433 | 71 | 1322 |
| 12.716 | 6.956 | 485 | 6110 | 28.687 | 3.1094 | 236 | 6361 |
| 13.584 | 6.5132 | 693 | 10117 | 28.93 | 3.0838 | 172 | 6511 |
| 14.225 | 6.2214 | 171 | 2300 | 29.652 | 3.0103 | 144 | 1939 |
| 15.27 | 5.7978 | 423 | 6239 | 31.025 | 2.8802 | 189 | 6158 |
| 15.753 | 5.6211 | 232 | 3565 | 31.73 | 2.8178 | 133 | 2399 |
| 17.51 | 5.0607 | 1089 | 16119 | 32.559 | 2.7479 | 232 | 3563 |
| 18.374 | 4.8248 | 614 | 8595 | 33.58 | 2.6666 | 91 | 2180 |
| 18.898 | 4.6922 | 346 | 5511 | 33.938 | 2.6394 | 87 | 2167 |
| 19.278 | 4.6005 | 2019 | 26612 | 35.033 | 2.5593 | 72 | 1734 |
| 19.916 | 4.4544 | 1280 | 21628 | 35.512 | 2.5258 | 116 | 3600 |
| 20.543 | 4.32 | 1524 | 24239 | 36.225 | 2.4778 | 72 | 749 |
| 21.474 | 4.1346 | 1112 | 16011 | 36.8 | 2.4404 | 46 | 686 |
| 22.018 | 4.0338 | 929 | 29364 | 37.493 | 2.3968 | 72 | 1084 |
| 22.623 | 3.9273 | 670 | 24897 | 38.49 | 2.337 | 39 | 1383 |
| 23.078 | 3.8508 | 579 | 9599 | 38.769 | 2.3208 | 59 | 1706 |

SOLVATES AND POLYMORPHS OF RITONAVIR AND METHODS OF MAKING AND USING THE SAME

RELATED APPLICATIONS

This application claims benefit to U.S. Provisional Patent Application No. 60/377,211 filed May 3, 2002, which is hereby incorporated by reference.

1. FIELD OF INVENTION

This invention relates to crystal forms of Ritonavir, methods of making and using the same, and pharmaceutical compositions comprising the same.

2. BACKGROUND OF THE INVENTION

Many compounds can exist in different crystal forms, or polymorphs. Individual polymorphs can exhibit different physical, chemical, and spectroscopic properties. For example, certain polymorphs may be more readily soluble in particular solvents, may flow more readily, or may compress more easily than others. See, e.g., P. DiMartino, et al., *J. Thermal Anal.*, 48:447–458 (1997). In the case of drugs, certain forms may be more bioavailable than others, while others may be more stable under certain manufacturing, storage, and biological conditions. This is particularly important from a regulatory standpoint, since drugs are approved by agencies such as the United States Food and Drug Administration ("FDA") only if they meet exacting purity and characterization standards. Indeed, the regulatory approval of one polymorph of a compound, which exhibits certain solubility and physico-chemical (including spectroscopic) properties, typically does not imply the ready approval of other polymorphs of that same compound.

One compound, which has received a lot of attention in connection with polymorphism, is Ritonavir. Ritonavir is chemically named 10-hydroxy-2-methyl-5-(1-methylethyl)-1-[2-(1-methylethyl)-4-thiazolyl]-3,6-dioxo-8,11-bis(phenylmethyl)-2,4,7,12-tetraazatridecan-13-oic acid, 5-thiazolylmethyl ester, [5S-(5R*,8R*,10R*,11R*)], and has the following structural formula:

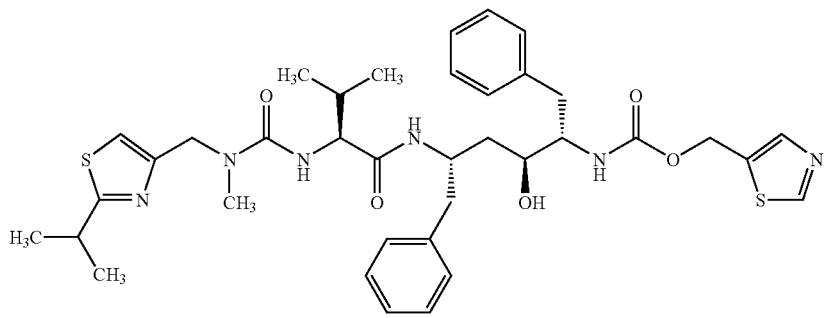

Ritonavir is an inhibitor of the HIV-1 and HIV-2 proteases with in vitro and in vivo activity against the Human Immunodeficiency Virus ("HIV"), and is presently sold in a soft gelatin capsule dosage form for oral administration under the trade name NORVIR® (Abbott Laboratories, North Chicago, Ill. USA). NORVIR® is indicated for use in combination with other antiretroviral agents for the treatment of HIV-infection. PHYSICIANS' DESK REFERENCE, 487–492 (56th ed., 2002). The combination of Ritonavir and Lopinavir is sold in a capsule dosage form for oral administration under the trade name KALETRA™, which is also indicated for use in combination with other antiretroviral agents for the treatment of HIV-infection. Id. at 471–478.

During the development and initial manufacture of Ritonavir, only one crystal form was identified. Bauer, J., et al., *Pharm. Res.*, 18(6):859–866 (2001). Because Ritonavir is not bioavailable in that form, however, the initially marketed oral formulations that comprised it contained Ritonavir dissolved in a semi-solid, waxy matrix filled into capsules. About two years after the initial marketing of NORVIR®, a second crystal form of Ritonavir was discovered; its presence in the capsule formulation caused the product to fail the dissolution specification mandated by the regulatory agencies. Id. As it later turned out, this new form, which is referred to as "Form II," was supersaturated in the hydroalcoholic solutions used in the drug formulations, even though the originally known form, which is now referred to as "Form I," was not. The sudden appearance of the significantly less soluble Form II prevented the further manufacture of the original NORVIR® formulations, and seriously threatened the supply of the drug. Id. At some considerable cost, a new formulation of NORVIR® was eventually developed.

Until now, only two crystalline forms of Ritonavir—Forms I and II—were known. Id.; Chemburkar, S. R., et al., *Organic Process Res. Dev.*, 4:413–417 (2000) ("Chemburkar"). Form I has a melting point of 122° C.; Form II has a melting point of 125° C. Chemburkar et al.

A need exists for other crystalline forms of Ritonavir, and bioavailable crystalline forms in particular. A need also exists for crystalline forms of the drug that can be used to more readily manufacture Forms I and II. Forms of Ritonavir are also desired which, when combined with other drugs, can be used to provide combination therapies that are more effective and/or better tolerated than those currently in use.

HIV infection is often treated using combination therapies, wherein two or more pharmaceutically active compounds are administered to the patient (e.g., together as a "drug cocktail"). Current therapies for HIV infection focus on inhibiting the activity of viral enzymes that are critical in the life cycle of the virus, such as reverse transcriptase and protease. Antiretrovirals that are presently in use are generally grouped into three classes: nucleoside reverse transcriptase inhibitors ("NRTIs"); non-nucleoside reverse transcriptase inhibitors ("NNRTIs"); and protease inhibitors ("PIs"). Combination therapies using such compounds have been shown to reduce the incidence of opportunistic infections and to increase survival time. It is possible that these and other benefits of combination therapies may be further improved by the use of new crystalline forms of Ritonavir.

3. SUMMARY OF THE INVENTION

This invention encompasses novel solvates and crystal polymorphs of Ritonavir. Specific solvates of the compound include a formamide solvate and a partially desolvated formamide solvate. All of the novel forms exhibit physical and spectroscopic characteristics that differ markedly from those of Forms I and II.

The invention further encompasses methods of making novel forms of Ritonavir, as well as methods of making previously known forms. Also encompassed by the invention are methods of using the novel forms of Ritonavir in the treatment of diseases, such as HIV-infection, and for enhancing the pharmacokinetic profiles of other pharmaceutically active compounds. Pharmaceutical compositions and unit dosage forms comprising novel forms of Ritonavir are also encompassed by the invention.

3.1. BRIEF DESCRIPTION OF THE FIGURES

Aspects of the invention can be understood with reference to the following non-limiting figures.

Figure 1:
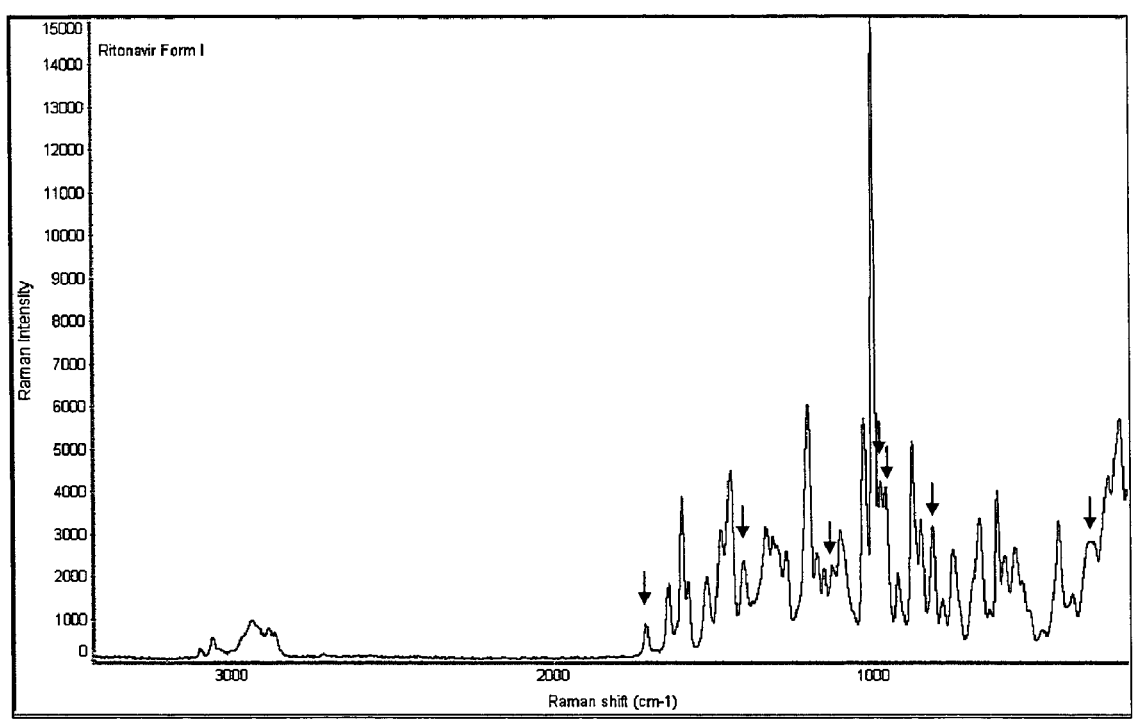
FIG. 1 is a Raman spectrum of Ritonavir Form I in the solid state.
Figures 2A, 2B:
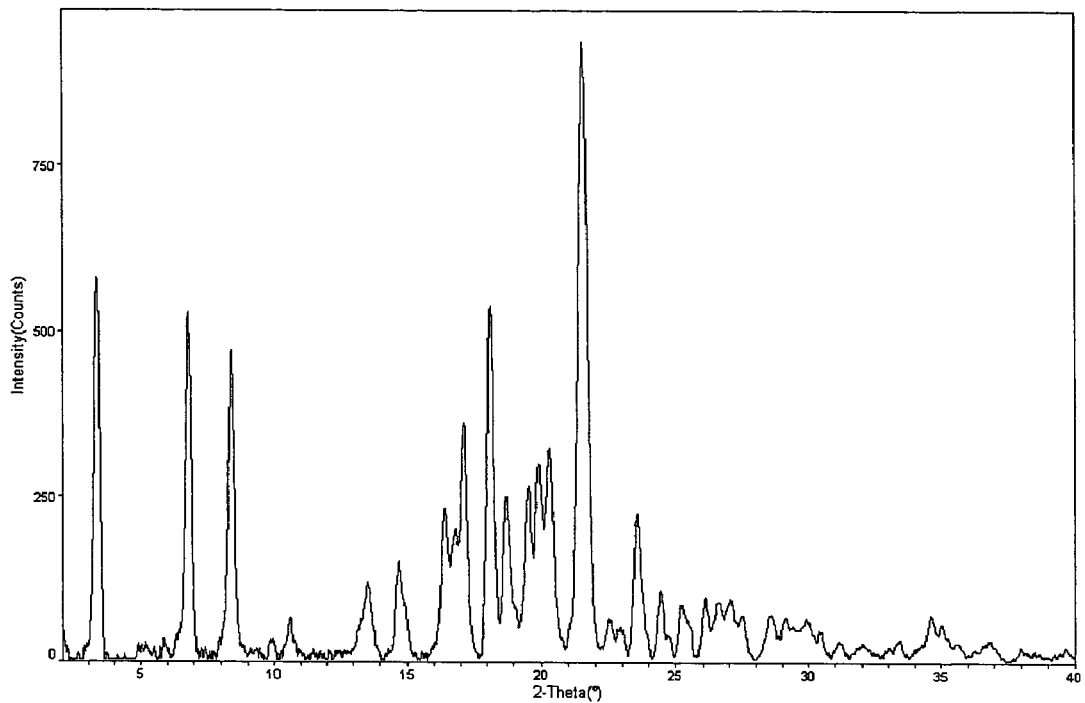
FIG. 2A is a powder X-ray diffraction pattern of Ritonavir Form I, and FIG. 2B contains a peak table for that diffraction pattern.
Figure 3:
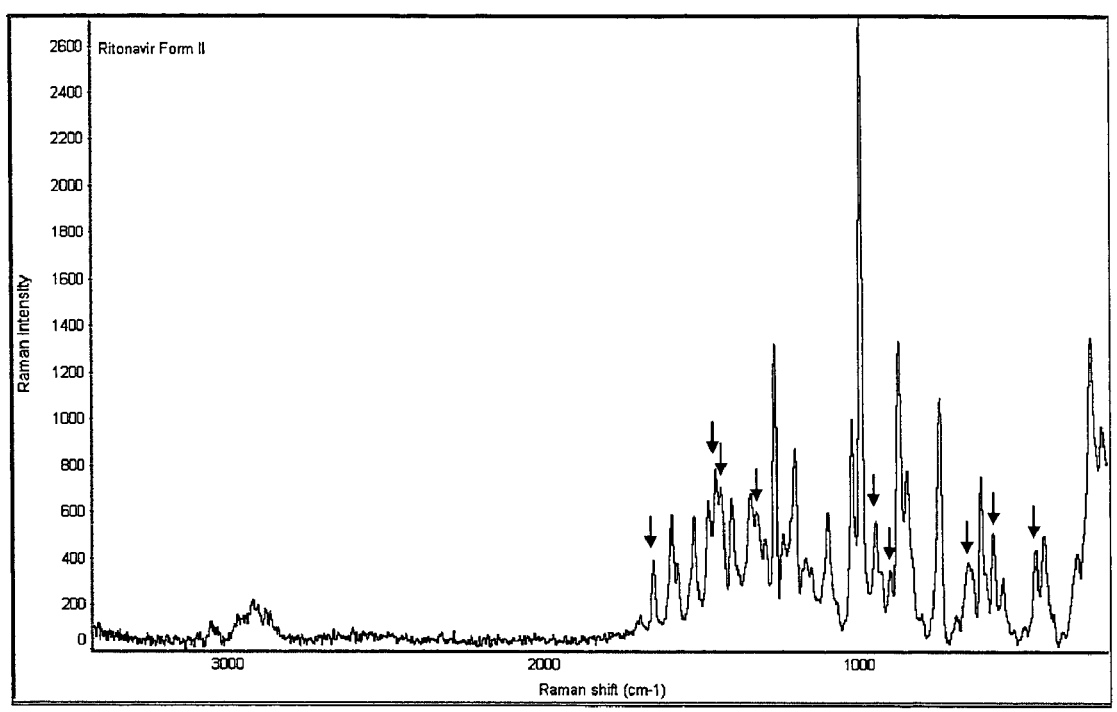

FIG. 3 contains a Raman spectrum of Ritonavir Form II in the solid state.

Figures 4A, 4B:
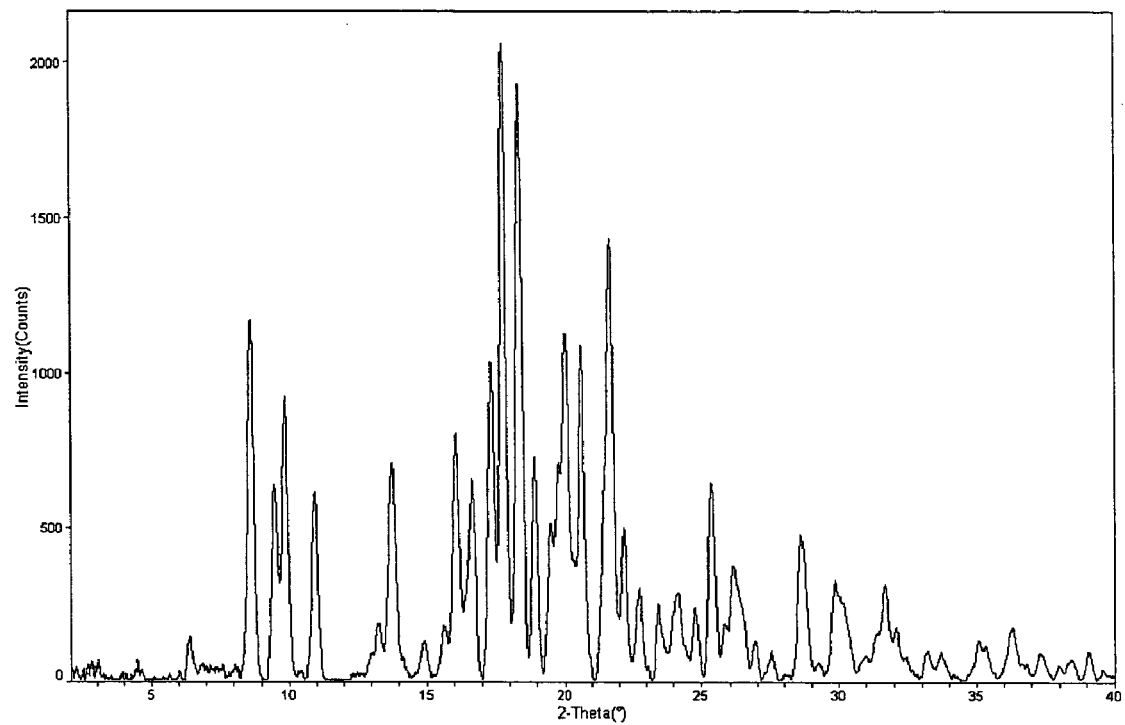

FIG. 4A is a powder X-ray diffraction pattern of Ritonavir Form II, and FIG. 4B contains a peak table for that diffraction pattern.

Figure 5:
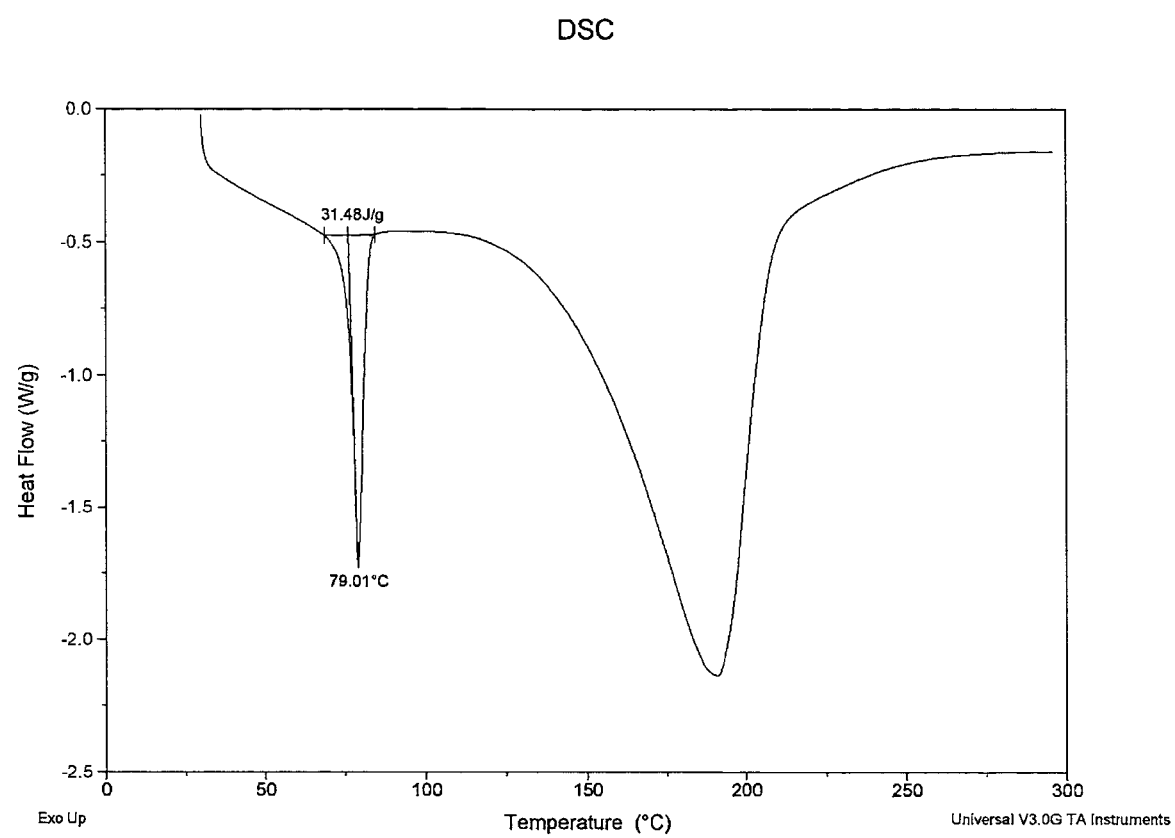

FIG. 5 is a DSC trace of Ritonavir Form III.

Figure 6:
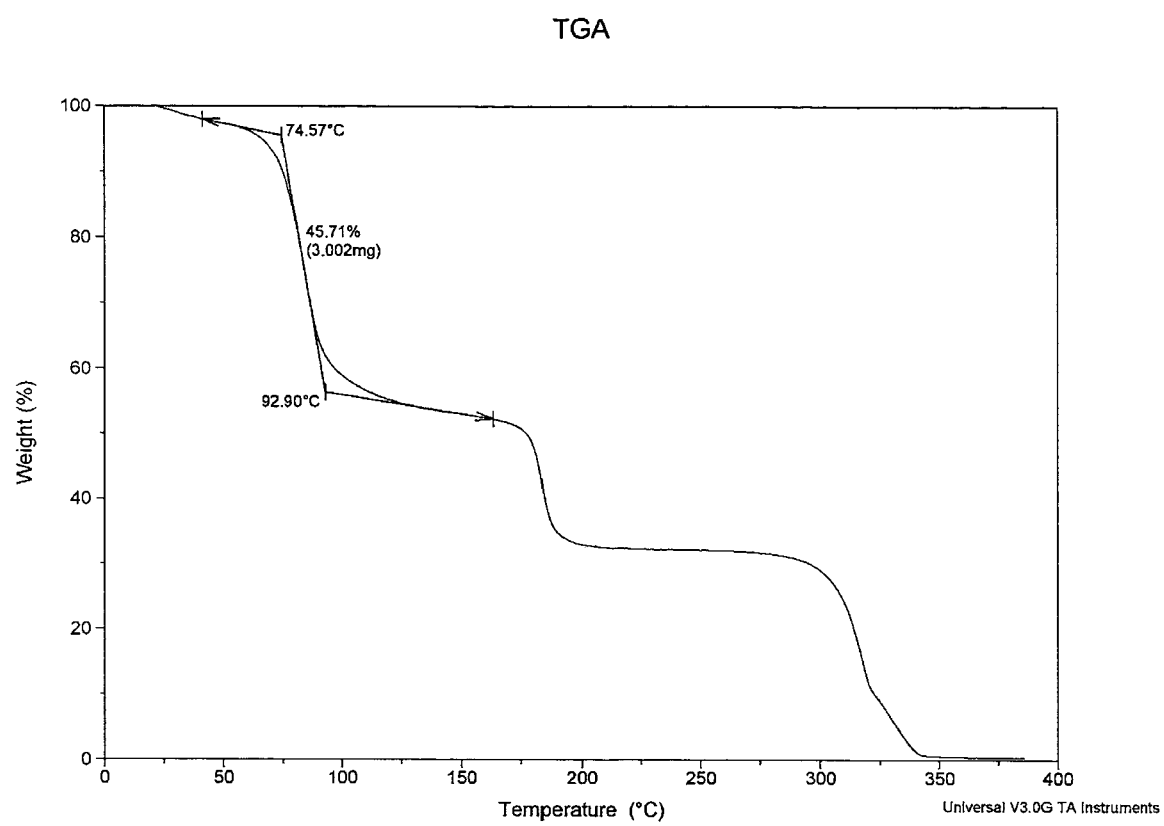

FIG. 6 is a TGA trace of Ritonavir Form III.

Figure 7:
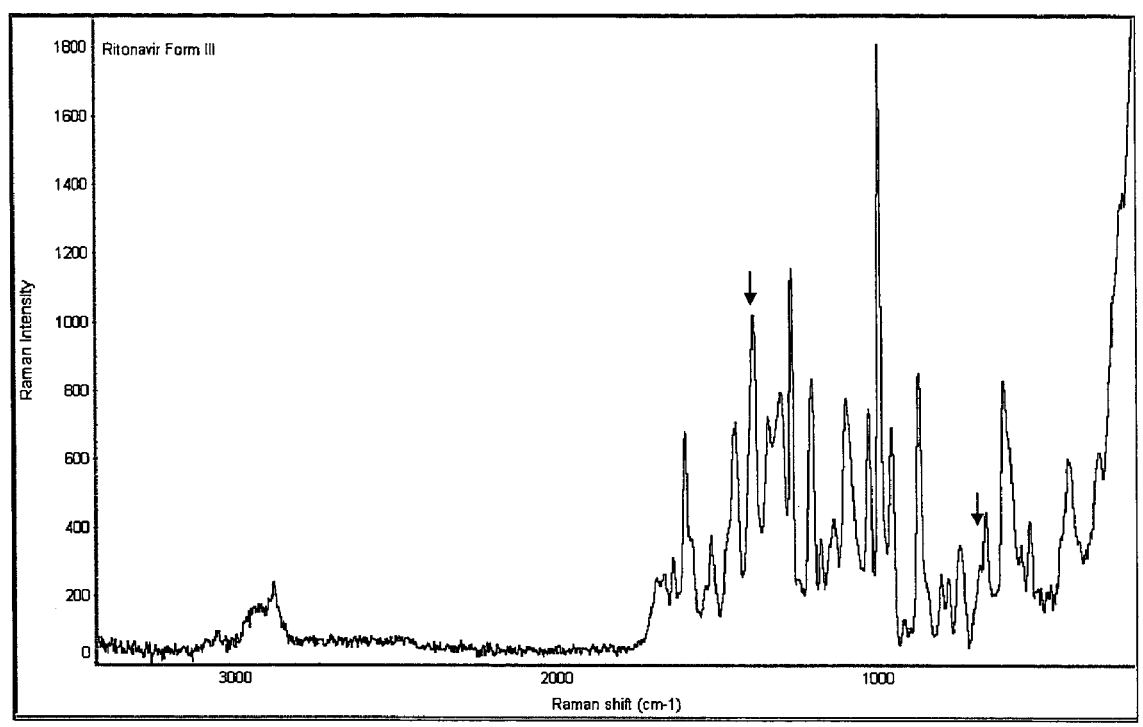

FIG. 7 is a Raman spectrum of Ritonavir Form III in the solid state.

Figures 8A, 8B:
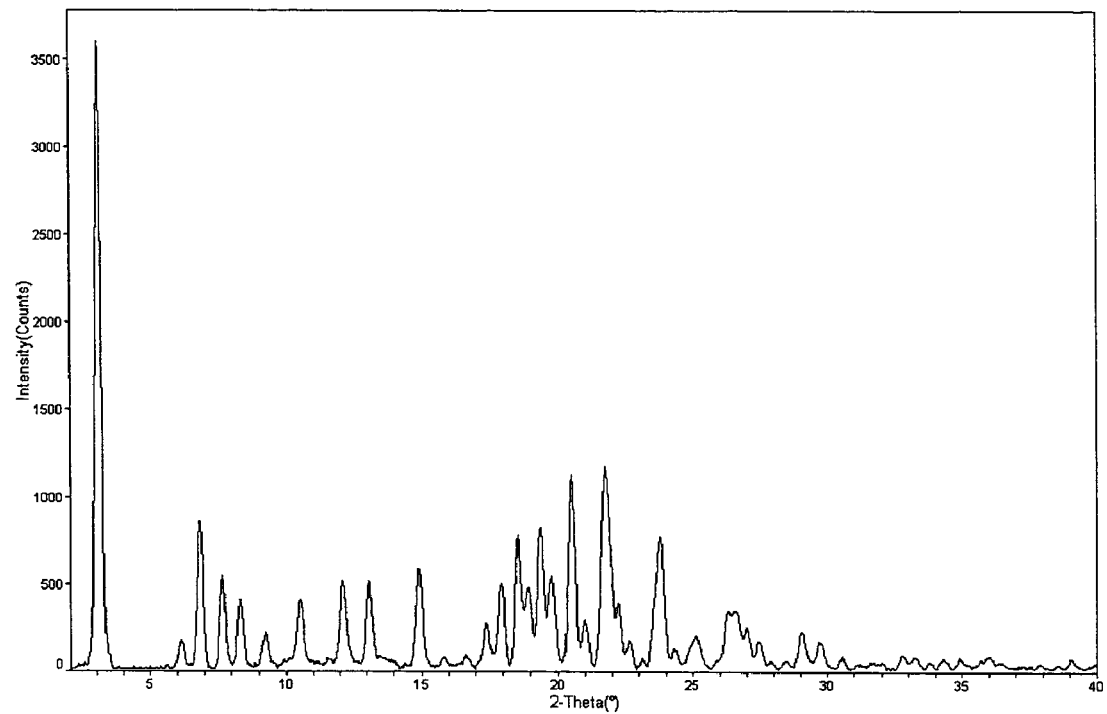

FIG. 8A is a powder X-ray diffraction pattern of Ritonavir Form III, and FIG. 8B contains a peak table for that diffraction pattern.

Figure 9:
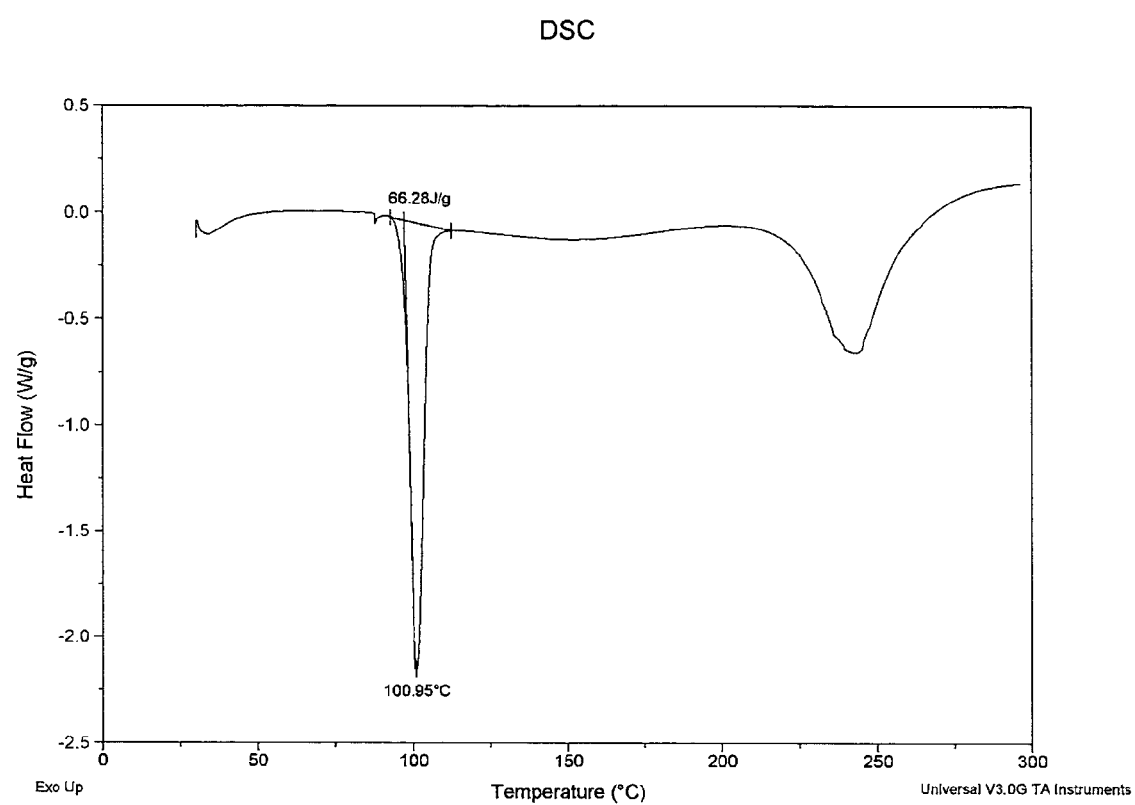

FIG. 9 is a DSC trace of Ritonavir Form IV.

Figure 10:
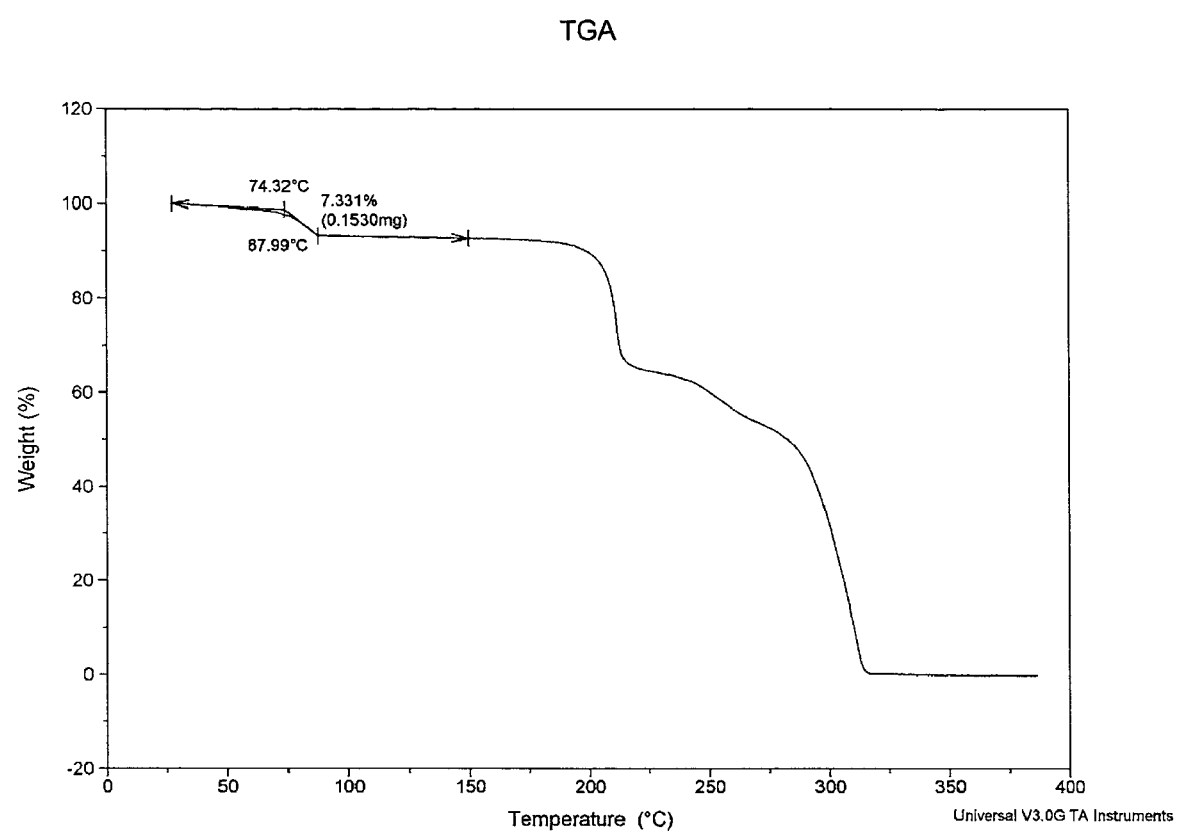

FIG. 10 is a TGA trace of Ritonavir Form IV.

Figure 11:
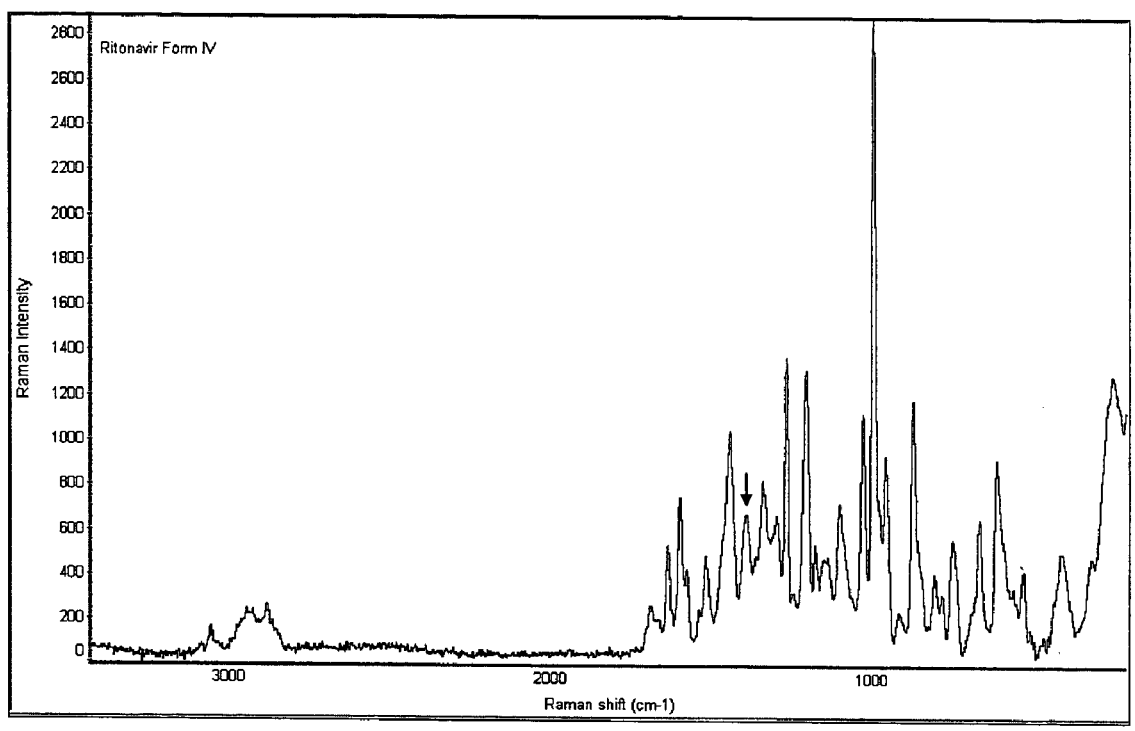

FIG. 11 is a Raman spectrum of Ritonavir Form IV in the solid state.

Figures 12A, 12B:
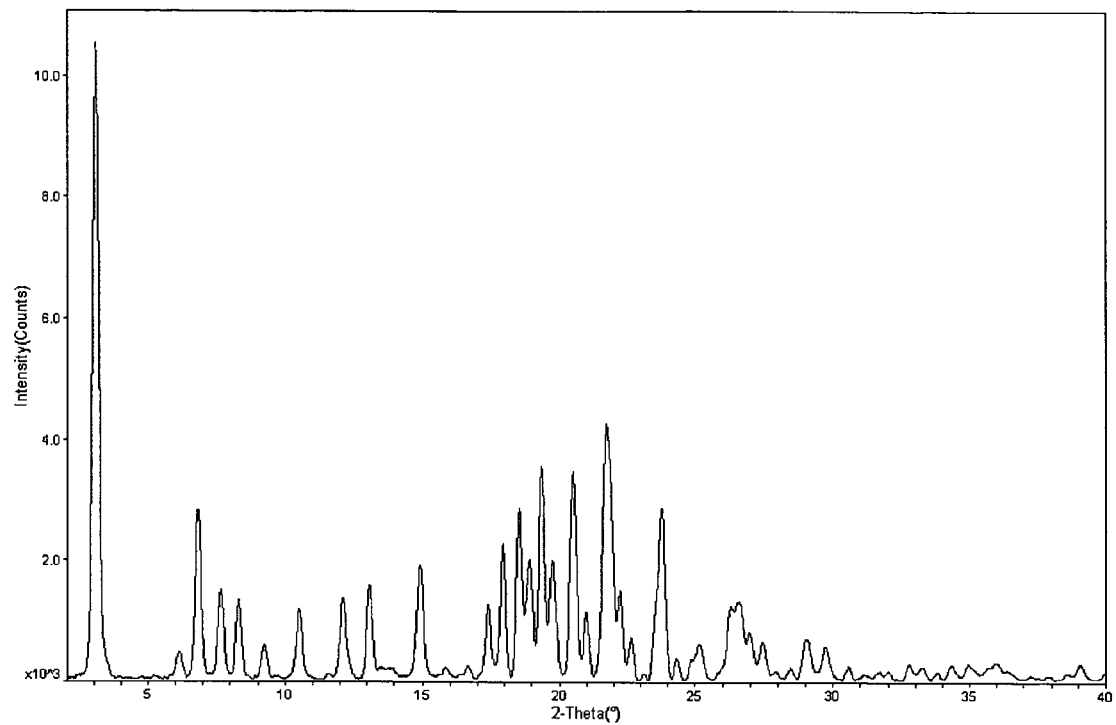

FIG. 12A is a powder X-ray diffraction pattern of Ritonavir Form IV, and FIG. 12B contains a peak table for that diffraction pattern.

Figure 13:
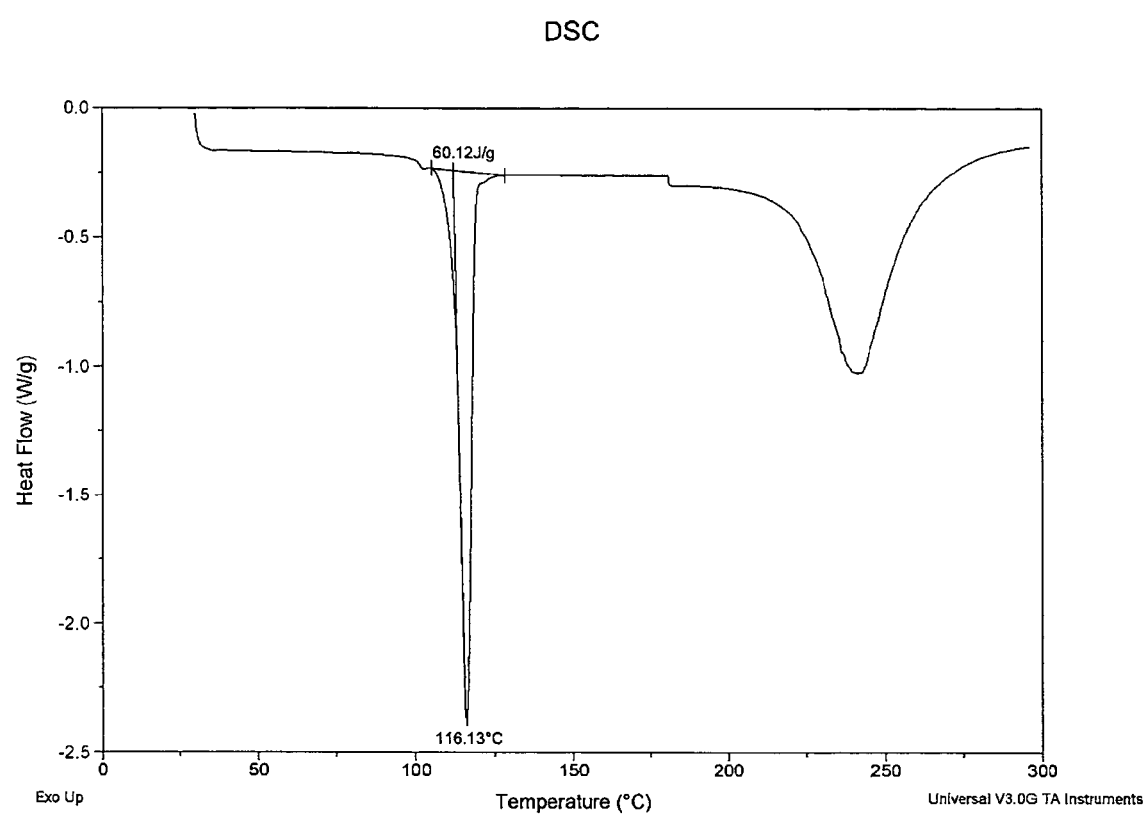

FIG. 13 is a DSC trace of Ritonavir Form V.

Figure 14:
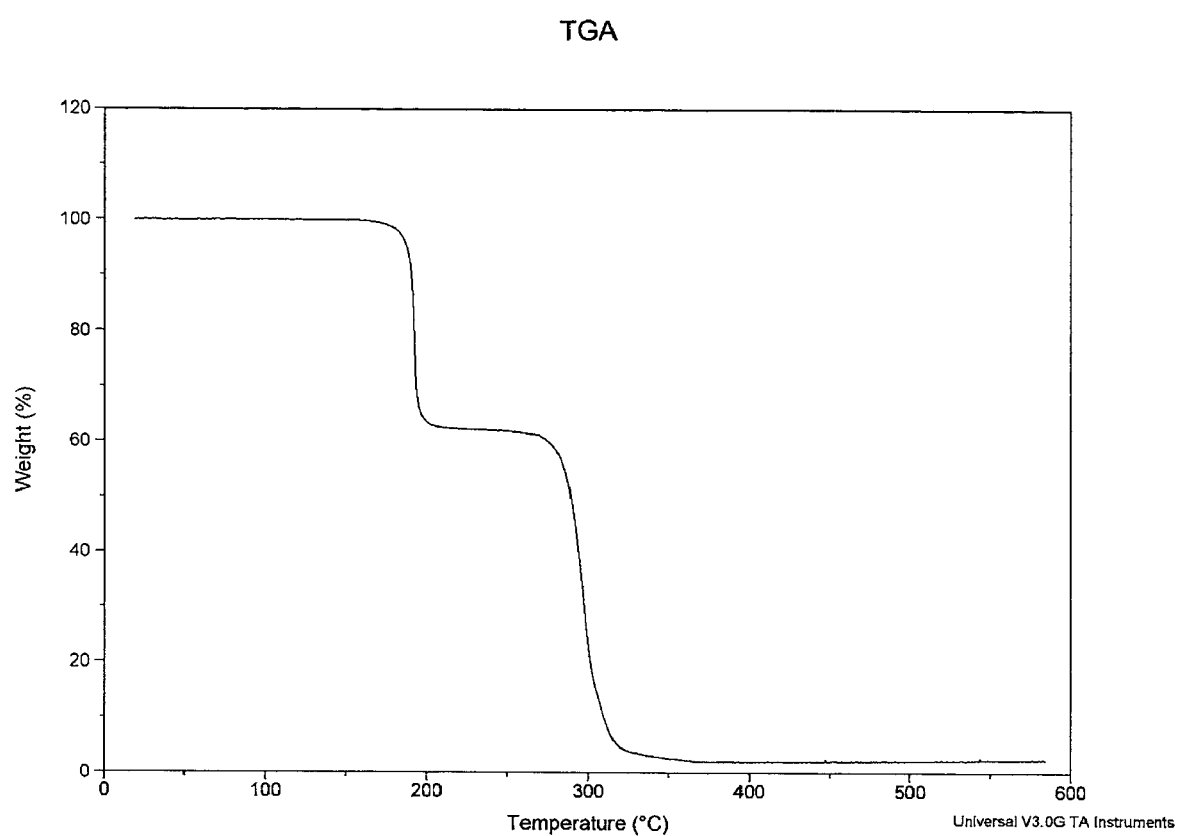

FIG. 14 is a TGA trace of Ritonavir Form V.

Figure 15:
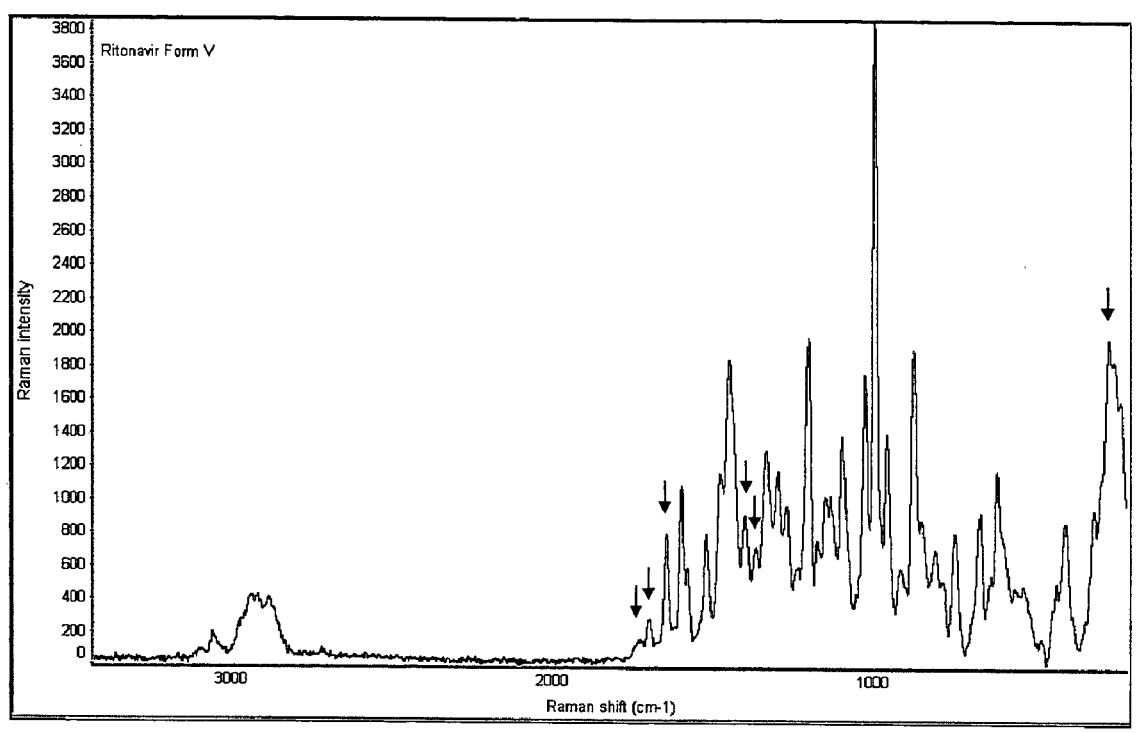

FIG. 15 is a Raman spectrum of Ritonavir Form V in the solid state.

Figures 16A, 16B:
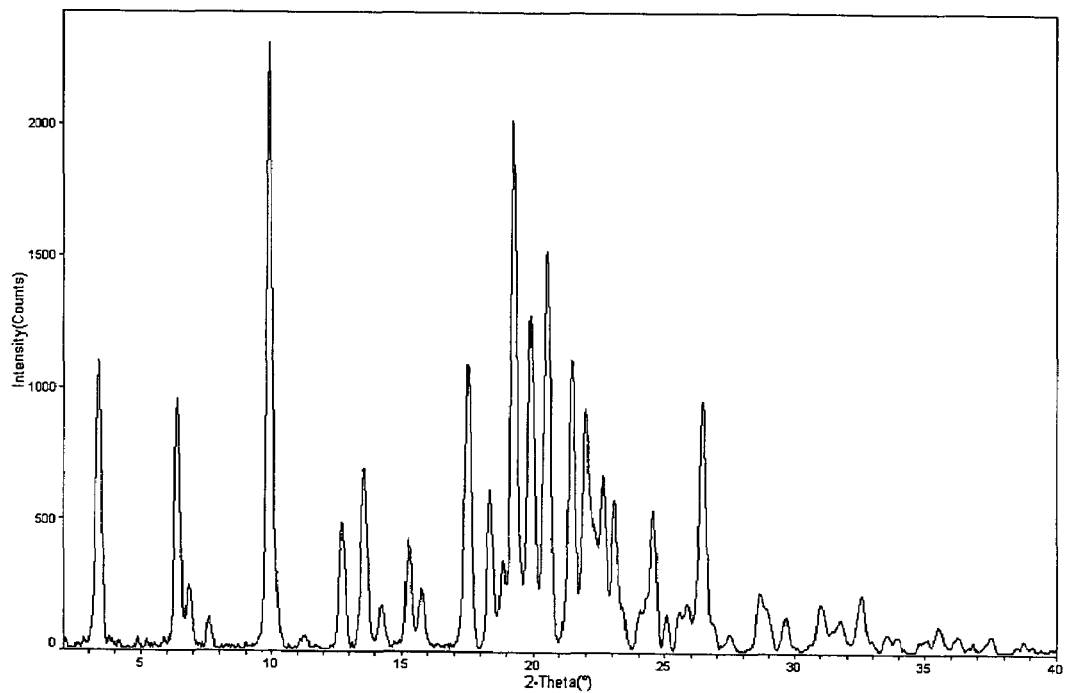

FIG. 16A is a powder X-ray diffraction pattern of Ritonavir Form V, and FIG. 16B contains a peak table for that diffraction pattern.

Figure 17:
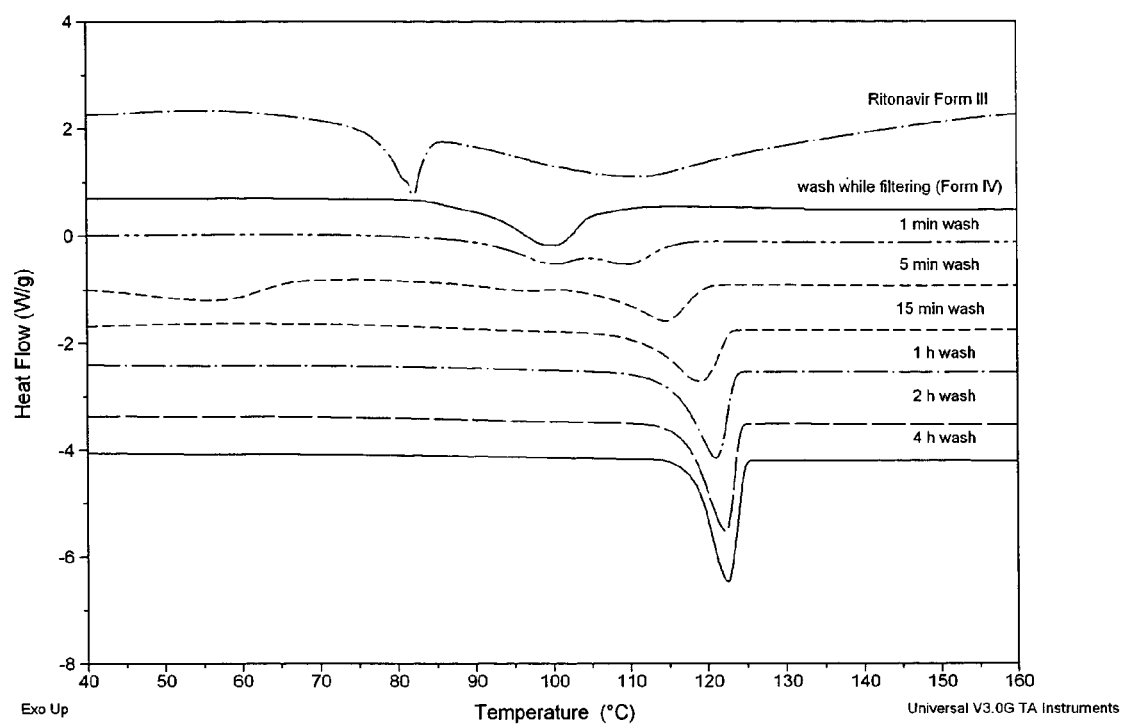

FIG. 17 shows, by DSC trace, the conversion of Ritonavir Form III to Form IV, and subsequently to Form I while being washed or incubated in aqueous media.

Figure 18:
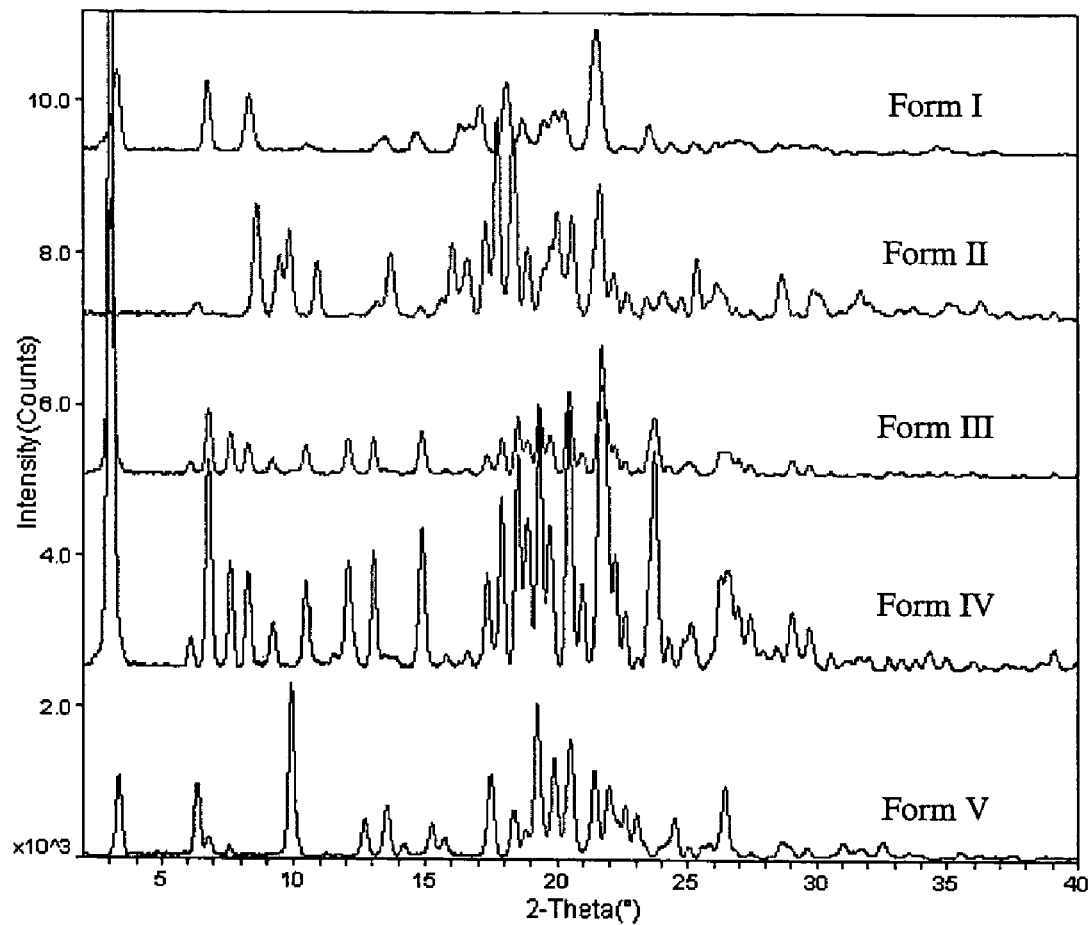

FIG. 18 provides a comparison of powder X-ray diffraction patterns of Ritonavir Forms I, II, III, IV, and V.

Figure 19:
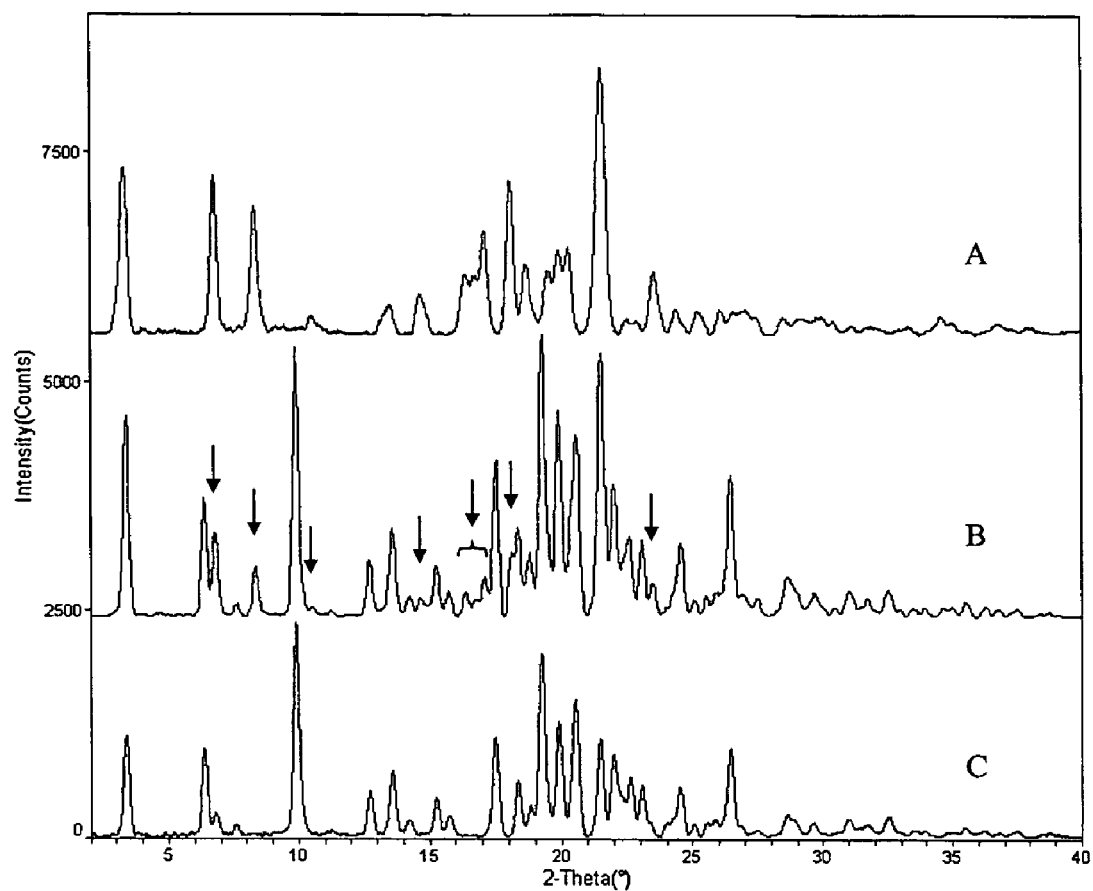

FIG. 19 shows the effect of leaving Ritonavir Form V in the crystallization mixture for about 16 hours at 5° C. In particular: (A) is a representative X-ray diffraction pattern of Ritonavir(I); (B) is an X-ray diffraction pattern of a sample of Ritonavir(V) after being left in the crystallization mixture for approximately 16 hours, with arrows indicating peaks that signify the presence of Ritonavir(I); and (C) is a representative X-ray diffraction pattern of Ritonavir(V).

Figure 20:
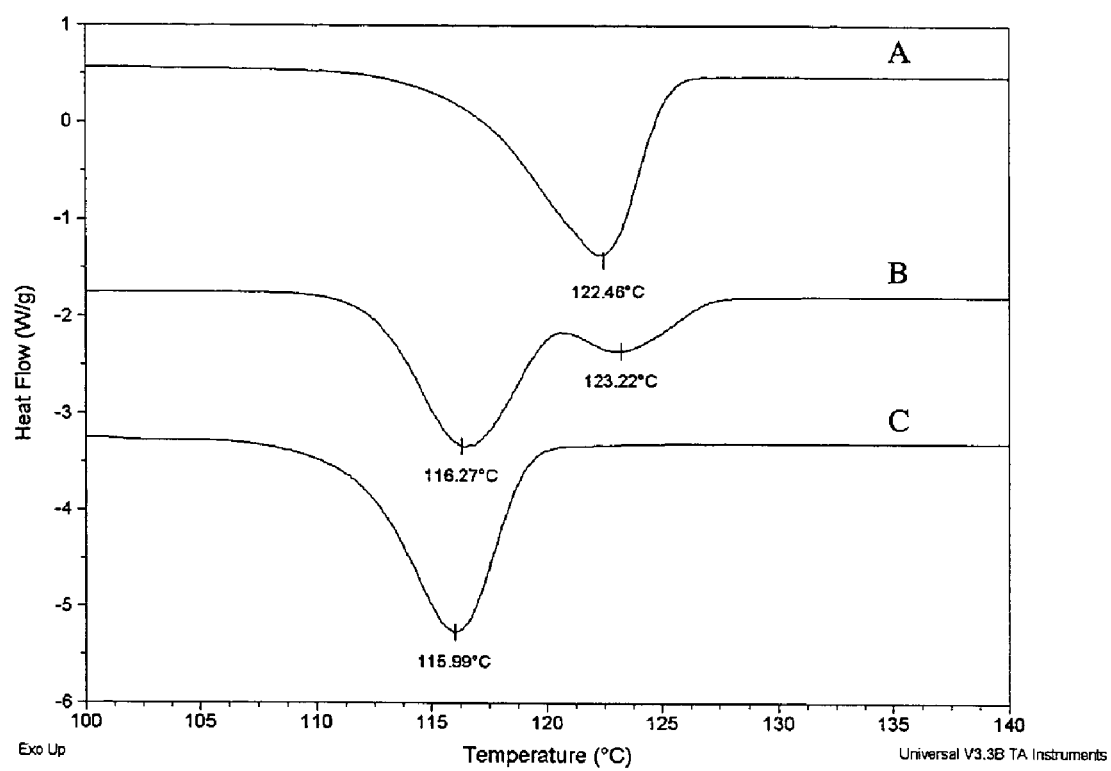

FIG. 20 also shows the effect of leaving Ritonavir Form V in the crystallization mixture for about 16 hours at 5° C. In particular: (A) provides a DSC trace of Ritonavir(I); (B) provides a DSC trace of a sample of Ritonavir(V) after being left in the crystallization mixture for approximately 16 hours, wherein two peaks are observed corresponding to Forms I and V; and (C) is a representative DSC trace of Ritonavir(V).

4. DETAILED DESCRIPTION OF THE INVENTION

This invention is based, in part, on a discovery that the protease inhibitor ("PI") Ritonavir can be obtained in novel crystalline forms. Advantageously, these new forms have lower melting points than previously known forms of Ritonavir (i.e., Forms I and II), which have poor bioavailability, and may thus be used to provide improved dissolution of Ritonavir. Forms of this invention may also be used to enhance the pharmacokinetics of other drugs (e.g., retroviral agents and reverse transcriptase inhibitors). The new forms of Ritonavir may also be used as intermediates in the manufacture of Forms I and II, as well as in the manufacture of pharmaceutical compositions and dosage forms comprising Ritonavir (e.g., dosage forms comprising dissolved Ritonavir). A further advantage of this invention is that methods of preparing the novel forms disclosed herein can be used to prepare those forms on a variety of scales, from microgram to milligram, gram, and even kilogram quantities.

A first embodiment of the invention encompasses what is referred to herein as "Ritonavir Form III" or "Ritonavir (III)." Ritonavir(III) has a melting point in the range of from about 78° C. to about 82° C., as exemplified by the Differential Scanning Calorimetry ("DSC") trace of the form shown in FIG. 5, which shows a melting point of about 79° C. A typical Thermal Gravimetric Analysis ("TGA") trace of Ritonavir(III) is provided in FIG. 6. Typical Raman spectra and powder X-ray diffraction patterns of Ritonavir(III) are provided in FIGS. 7 and 8, respectively. Without being limited by theory, it is believed that Ritonavir(III) is a formamide solvate of Ritonavir.

Another embodiment of the invention encompasses what is referred to herein as "Ritonavir Form IV" or "Ritonavir (IV)." Ritonavir(IV) has a melting point in the range of from about 97° C. to about 101° C., as exemplified by the DSC trace of the form shown in FIG. 9, which shows a melting point of about 101° C. A typical TGA trace of Ritonavir(IV) is provided in FIG. 10. Typical Raman spectra and powder X-ray diffraction patterns of Ritonavir(IV) are provided in FIGS. 11 and 12, respectively. Without being limited by theory, it is believed that Ritonavir(IV) is a partially desolvated formamide solvate of Ritonavir.

Another embodiment of the invention encompasses what is referred to herein as "Ritonavir Form V" or "Ritonavir (V)." Ritonavir(V) has a melting point in the range of from about 114° C. to about 118° C., as exemplified by the DSC spectrum of the form shown in FIG. 13, which shows a melting point of about 116° C. A typical TGA trace of Ritonavir(V) is provided in FIG. 14. Typical Raman and powder X-ray diffraction spectra of Ritonavir(V) are provided in FIGS. 15 and 16, respectively. Without being limited by theory, it is believed that Ritonavir(V) is a polymorph of Ritonavir Forms I and II.

Another embodiment of the invention encompasses a method of making Ritonavir(III), which comprises dissolving Ritonavir in a solvent system comprised of formamide and an immiscible or partially miscible solvent to provide a mixture, and reducing the solubility of Ritonavir in the mixture under conditions sufficient to provide Ritonavir(III). A specific solvent system is a binary solvent system. Preferred immiscible or partially miscible solvents include, but are not limited to, toluene, butyl acetate, and acetone. In a specific method, the solubility of Ritonavir(III) is reduced by cooling the mixture. In another method, the solubility of Ritonavir(III) is reduced by evaporating some of the mixture. In any of these methods, Ritonavir(III) can be crystallized from static layers of the solvents, or while the solvents are vigorously stirred (e.g., with a non-reactive magnetic stirrer).

Another embodiment of the invention encompasses a method of making Ritonavir(IV), which comprises partially desolvating Ritonavir(III) to an extent sufficient to yield Ritonavir(IV). In a specific method, Ritonavir(III) is contacted with an aqueous medium in an amount and for a time sufficient to form Ritonavir(IV).

Another embodiment of the invention encompasses a method of making Ritonavir(V), which comprises drying Ritonavir(III) in a vacuum in an amount and for a time sufficient to form Ritonavir(IV). In a specific method, Ritonavir(III) is placed in a vacuum oven to dry for about 38 hours.

Another embodiment of the invention encompasses a method of making Ritonavir(V), which comprises dissolving Ritonavir in a solvent system comprised of an acetate (e.g., an alkyl acetate) and acetonitrile to produce a mixture, and reducing the solubility of Ritonavir in the mixture under conditions sufficient to provide Ritonavir(V). A specific solvent system is a binary solvent system. Specific acetates include, but are not limited to, butyl acetate, isobutyl acetate, and isopropyl acetate. A preferred ratio of acetate to acetonitrile is from about 50:50 to about 75:25 acetate:acetonitrile. In a specific method, the solubility of Ritonavir(V) is reduced by cooling the mixture. In another method, the solubility of Ritonavir(V) is reduced by partially evaporating solvent from the mixture.

Another embodiment of the invention encompasses a method of treating, ameliorating, or managing a disease or condition associated with the proteolytic activity of HIV protease, which comprises administering to a patient in need of such treatment or prevention a therapeutically or prophylactically effective amount of Ritonavir(III), Ritonavir(IV), or Ritonavir(V). Preferred methods comprise the administration of Ritonavir(V).

Another embodiment of the invention encompasses a method for improving the pharmacokinetics of a pharmacologically active compound, which comprises administering to a human in need of the pharmacologically active compound a combination of a therapeutically effective amount of Ritonavir(III), (IV), or (V), or a pharmaceutically acceptable salt thereof, and a therapeutically effective amount of the pharmacologically active compound, or a pharmaceutically acceptable prodrug, salt, hydrate, solvate, or polymorph thereof, wherein the pharmacologically active compound is metabolized by cytochrome P450 monooxygenase(s). In a particular embodiment, the pharmacologically active compound is an antiretroviral compound. Examples of antiretroviral compounds include, but are not limited to, PIs, NRTIs, and NNRTIs.

Another embodiment of the invention encompasses pharmaceutical compositions and dosage forms of Ritonavir(III), Ritonavir(IV), and Ritonavir(V). Preferred compositions and dosage forms comprise Ritonavir(V), optionally in combination with another pharmacologically active compound (e.g., a second HIV protease inhibitor or one or more HIV reverse transcriptase inhibitors).

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives of pharmacologically active compounds that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Prodrugs can typically be prepared using well-known methods, such as those described in 1 BURGER'S MEDICINAL CHEMISTRY AND DRUG DISCOVERY, 172–178, 949–982 (Manfred E. Wolff ed., 5$^{th}$ ed. 1995), and DESIGN OF PRODRUGS (H. Bundgaard ed., Elsevier, N.Y. 1985).

As used herein and unless otherwise indicated, the terms "biohydrolyzable amide," "biohydrolyzable ester," "biohydrolyzable carbamate," "biohydrolyzable carbonate," "biohydrolyzable ureide," "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, lower acyloxyalkyl esters (such as acetoxylmethyl, acetoxyethyl, aminocarbonyloxymethyl, pivaloyloxymethyl, and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkyl esters, choline esters, and acylamino alkyl esters (such as acetamidomethyl esters). Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein and unless otherwise indicated, the term "pharmaceutically acceptable salts" refer to salts prepared from pharmaceutically acceptable non-toxic acids or bases including inorganic acids and bases and organic acids and bases. Suitable pharmaceutically acceptable base addition salts for the compound of the present invention include metallic salts made from aluminum, calcium, lithium, magnesium, potassium, sodium and zinc or organic salts made from lysine, N,N*-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts.

4.1. Preparation of Solvents and Polymorphs

This invention evidences the power and utility of the methods and systems collectively referred to as CRYSTAL-MAX™, which are described in U.S. provisional patent application No. 60/221,539, filed Jul. 28, 2000; U.S. patent application Ser. No. 09/756,092, filed Jan. 8, 2001; International Publication WO01/51919; U.S. provisional patent application No. 60/318,157, filed Sep. 7, 2001; U.S. provisional patent application No. 60/318,138, filed Sep. 7, 2001; U.S. provisional patent application No. 60/318,152, filed Sep. 7, 2001; and U.S. provisional patent application No. 60/366,523, filed Mar. 22, 2002, all of which are incorporated herein by reference.

Using the CRYSTALMAX™ methods and systems, it was discovered that Ritonavir(III) can be crystallized from solvent systems (e.g., binary systems) comprised of formamide and an immiscible or partially miscible solvent. In particular, it was discovered that after Ritonavir is dissolved in such a solvent system at an elevated temperature (e.g., about 70° C.), the slow cooling of the resulting mixtures (e.g., at a rate of about 5° C./minute until a temperature of about 5° C. is reached) typically yields crystals of Ritonavir(III), which can be isolated by filtration and optionally dried by air. Specific immiscible or partially miscible solvents include, but are not limited to, toluene, butyl acetate, and acetone. Specific solvent systems comprise about 75 volume percent form amide.

Ritonavir(IV) can be prepared from Ritonavir(III). In a particular method, Ritonavir(III) is contacted with an aqueous medium for an amount of time sufficient to effect the change. For example, Ritonavir(III) placed on a vacuum filter can be washed with deionized water, thereby providing Ritonavir(IV). When Ritonavir(IV) is exposed to an aqueous environment for an extended amount of time (e.g., about 15 to about 60 minutes), it converts to Ritonavir Form I. Prolonged exposure of Ritonavir(IV) to an aqueous environment converts the compound to Ritonavir Form II.

Ritonavir(V) is readily prepared from solvent systems (e.g., binary solvent systems) comprised of an acetate and acetonitrile. In particular, it was discovered that after Ritonavir is dissolved in such a solvent system at an elevated temperature (e.g., about 70° C.), the slow cooling of the resulting mixtures (e.g., at a rate of about 5° C./minute until a temperature of about 5° C. is reached) typically yields crystals of Ritonavir(V), which can be isolated by filtration and optionally dried by air. Specific solvent systems comprise from about 25 to about 50 volume percent acetonitrile. It was also found that prolonged incubation of Ritonavir(V) in the crystallization mixture provides Ritonavir Form I.

4.2. Methods of Treatment and Prevention

Compounds of the invention (e.g., Ritonavir(V)) can be used for the treatment or management of diseases and conditions associated with activity of HIV proteases. Examples of such diseases and conditions include, but are not limited to, HIV-infection.

As discussed herein, compounds of the invention are typically incorporated into pharmaceutical compositions, such as individual dosage forms suitable for administration by any of a variety of routes. The magnitude of a prophylactic or therapeutic dose of a pharmaceutical composition of the invention for the acute or chronic management of a disease will vary with the severity of the condition to be treated and the route of administration. The dose, and perhaps the dose frequency, will also vary according to age, body weight, response, and the past medical history of the individual patient. For example, the general recommended daily dose range for the treatment and/or prevention of the diseases, disorders, and/or conditions described herein using a pharmaceutical composition comprising Ritonavir as the active ingredient lie within the range of from about 100 mg to about 1200 mg, from 200 mg to about 1000 mg, and from 400 mg to about 800 mg twice daily by mouth. A preferred dose is about 600 mg Ritonavir twice daily. Dose titration schedules such as those published in connection with NORVIR® may be used to reduce or avoid adverse effects. See, e.g., PHYSICIANS' DESK REFERENCE, 487–492 ($56^{th}$ ed., 2002).

As with previously known forms of Ritonavir, those of the invention can be combined or adjunctively administered with other pharmacologically active compounds when used to treat or prevent diseases or conditions. For example, compounds of the invention can be administered in combination with other compounds or pharmaceutical agents for the treatment or prevention of infectious disease of HIV including, but not limited to, PIs, NRTIs, and NNRTIs. Examples of PIs include, but are not limited to, lopinavir, saquinavir, indinavir, nelfinavir, amprenavir, palinavir, lasinavir, tipranavir, and those disclosed in U.S. Pat. Nos. 6,284,767; 5,886,036; 5,846,987; and 5,635,523, all of which are incorporated herein by reference. Examples of NRTIs include, but are not limited to, zidovudine, zalcitabine, lamivudine, didanosine, abacavir, tidoxil, stavudine, adefovir, adefovir dipivoxil, fozivudine, and the like. Examples of NNRTIs (which may also include an agent having antioxidation activity) include, but are not limited to, delavirdine, efavirenz, immunocal, loviride, nevirapine, oltipraz, and the like.

Ritonavir reportedly inhibits, and is believed to be metabolized by, isoforms of cytochrome P450 monooxygenase, including without limitation CYP3A and CYP2D6. See, U.S. Pat. No. 6,037,157 and PHYSICIANS' DESK REFERENCE, 487–492 ($56^{th}$ ed., 2002). Consequently, when Ritonavir is co-administered with a second compound or pharmaceutical that is metabolized by one or more cytochrome P450 monooxygenases inhibited by Ritonavir, the pharmacokinetics of the second compound may be affected. For example, the clearance of the second compound may be slowed, and its blood level thereby increased. See, e.g., PHYSICIANS' DESK REFERENCE, 488–9, Tables 2 and 4 ($56^{th}$ ed., 2002). Because of its ability to affect the metabolism of other drugs (e.g., antiviral drugs), Ritonavir can be used to provide combination therapies that are particularly advantageous. In particular, Ritonavir can increase the pharmacological activity of a co-administered compound, allowing a reduction of its dose. The co-administration of Ritonavir may also increase the blood half-life of a co-administered compound such that its administration need not be as frequent or may occur by a different route (e.g., oral, instead of intravenous), thereby enhancing patient compliance. Ritonavir administration may also be used to improve the safety profile of the co-administered compound, as less of that compound may be needed to elicit its desired pharmacological (e.g., antiviral) effect.

Examples of drugs which are metabolized by cytochrome P450 monooxygenase(s) and which may benefit from the co-administration of the novel forms of Ritonavir disclosed herein include, but are not limited to, immunosuppressants, chemotherapeutic agents, antibiotics, antifungals, and HIV protease inhibitors. Examples of each include, but are not limited to, those disclosed in U.S. Pat. No. 6,037,157, the entirety of which is incorporated herein by reference. Because of the unique characteristics of the Ritonavir forms of this invention, their combination with other drugs may be used to provide drug cocktails that are uniquely safe and effective.

As the skilled clinician will readily recognize, the dose of Ritonavir, and perhaps the dosing regimen used for the treatment of a particular disease or condition with it, will likely be different when Ritonavir is used alone or in combination with other drugs. Guidance in connection with doses and dosing regimens may be obtained from clinical study data and packaging information available for previous forms of Ritonavir. See, e.g., PHYSICIANS' DESK REFERENCE, 487–492 ($56^{th}$ ed., 2002).

The term "therapeutically or prophylactically effective amount" when used to describe a method of the invention (e.g., a method of treating HIV-infection) encompasses the above described dosage amounts and dose frequency schedules.

Methods of the invention that are directed to the prevention, amelioration, or management of a disease, disorder, or condition comprise the administration of a form of Ritonavir to a patient at risk of suffering from the disease, disorder, or condition. In general, a qualified physician will readily be able to determine whether or not a given patient is at risk. For example, those of ordinary skill in the art are well aware of patient populations at risk of HIV-infection.

Any suitable route of administration can be employed to provide the patient with a therapeutically or prophylactically effective dose of an active ingredient. For example, oral, mucosal (e.g., nasal, sublingual, buccal, rectal, vaginal), parenteral (e.g., intravenous, intramuscular), transdermal, and subcutaneous routes can be employed. A preferred route of administration is oral.

4.3. Pharmeceutical Compositions and Dosage Forms

Pharmaceutical compositions and dosage forms of the invention comprise a compound of the invention (e.g., Ritonavir(V)), typically in combination with one or more pharmaceutically acceptable excipients, and optionally in combination with one or more additional pharmacologically active compounds. Examples of additional pharmacologically active compounds include, but are not limited to, PIs, NRTIs, and NNRTIs, such as those disclosed herein. Other additional pharmacologically active compounds include, but are not limited to, immunosuppressants, chemotherapeutic agents, antifungals, and antibiotics.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as hard gelatin, HPMC, starch, and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form suitable for mucosal administration may contain a smaller amount of active ingredient(s) than an oral dosage form used to treat the same indication. This aspect of the invention will be readily apparent to those skilled in the art. See, e.g., REMINGTON'S PHARMACEUTICAL SCIENCES, $18^{th}$ ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients can be accelerated by some excipients such as lactose, or when exposed to water. Active ingredients that comprise primary or secondary amines are particularly susceptible to such accelerated decomposition. Consequently, this invention encompasses pharmaceutical compositions and dosage forms that contain little, if any, lactose or other mono- or di-saccharides. As used herein, the term "lactose-free" means that the amount of lactose present, if any, is insufficient to substantially increase the degradation rate of an active ingredient.

Lactose-free compositions of the invention can comprise excipients that are well known in the art and are listed, for example, in the U.S. Pharmacopeia (USP) 25-NF20 (2002). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379–80. Water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials) with or without dessicants, blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise Ritonavir in an amount of from about 50 mg to about 1000 mg, preferably in an amount of from about 75 mg to about 750 mg, and most preferably in an amount of from about 100 mg to about 500 mg.

4.4.1. Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, REMINGTON'S PHARMACEUTICAL SCIENCES, $18^{th}$ ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, stabilizers, and disintegrating agents.

Because of their ease of administration, tablets, caplets, and capsules represent the most advantageous oral dosage unit forms, in which case solid excipients are employed. If desired, tablets and caplets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, stabilizers, disintegrants, surfactants (as wetting agents) and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Examples of surfactants as wetting agents or aids include, but are not limited to, sodium lauryl sulfate (SDS) and poloxamers (e.g., PLURONICS). The former is a solid while the latter are liquids and available in various grades (ex. 188, 237, etc.) based on molecular weight. The action of these agents in pharmacuetical compositions or formulation is particularly important as the oral dosage forms are ingested and drug release must take place in the body.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Specific dosage forms into which Ritonavir(III), Ritonavir (IV), and Ritonavir(V) can be incorporated, or which can be prepared using the forms of this invention, are disclosed in U.S. Pat. No. 6,232,333, which is incorporated herein by reference.

4.4.2. Delayed Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydroxypropyl methyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

4.4.3. Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

4.4.4. Transdermal, Topical, and Mucosal Dosage Forms

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., REMINGTON'S PHARMACEUTICAL SCIENCES, $16^{th}$ and $18^{th}$ eds., Mack Publishing, Easton Pa. (1980 & 1990); and INTRODUCTION TO PHARMACEUTICAL DOSAGE FORMS, $4^{th}$ ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., REMINGTON'S PHARMACEUTICAL SCIENCES, 16th and 18th eds., Mack Publishing, Easton Pa. (1980 & 1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

4.4.5. Kits

Typically, active ingredients of the invention are preferably not administered to a patient at the same time or by the same route of administration. This invention therefore encompasses kits which, when used by the medical practitioner, can simplify the administration of appropriate amounts of active ingredients to a patient.

A typical kit of the invention comprises a unit dosage form of Ritonavir(V) and a unit dosage form of a second pharmacologically active compound, such as an HIV protease inhibitor. A kit may further comprise a device that can be used to administer the active ingredient. Examples of such devices include, but are not limited to, syringes, drip bags, patches, and inhalers.

Kits of the invention can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

5. EXAMPLES

Certain aspects and embodiments of the invention are illustrated by the following non-limiting examples.

5.1. Example 1

Preparation of Ritonavir Form I

NORVIR-brand Ritonavir (Abbott Laboratories, North Chicago, Ill. USA) oral solution was used to obtain Ritonavir Form I. Specifically, approximately 240 mL of NORVIR solution (the contents of a normal prescription bottle, totaling about 19.2 g of Ritonavir) were placed into a 500 mL round bottom flask and vacuum-treated (pumping at high vacuum) for about 6 hours at room temperature on a slightly heated water bath to keep temperature constant. 50 mL of ethyl acetate was added to the viscous residue (dark orange in color).

The resulting solution was placed into a 2 liter flask and while stirring, diethyl ether was added to a final volume of about 1800 mL. The solution was stirred for 30 minutes at room temperature to allow precipitation to occur. The ether phase was poured through a 150 mL sintered glass, coarse frit funnel to clarify the ether. Successive aliquots of approx. 300 mL of filtrate were placed into a 500 mL round bottom flask and the solvent was removed by rotary evaporation in vacuo (water aspirator) until a slightly off-white residue remained.

Ether aliquots were added to the residue in the round bottom flask until all the ether had been evaporated. The final residue was transferred into a 500 mL Erlenmeyer flask and diluted with methylene chloride to a final volume of about 150 mL. A total of about 350 mL deionized water was added to the methylene chloride solution by gently pouring down the edge of the flask, while the solution was stirred by a magnetic stirbar on a stirplate at approximately 200 rpm.

After about 1.5 hours of stirring, the mixture was poured into a separatory funnel. After settling, the methylene chloride fraction (bottom layer) was separated into an Erlenmeyer flask, and allowed to dry over anhydrous sodium sulfate for 15 minutes (during which time the organic solvent went from opaque to clear).

After filtering the methylene chloride solution, the solvent was removed by rotary evaporation. The resulting residual syrup was placed in a −20° C. freezer overnight to allow crystals to form. The crystals were isolated, and then the solid compound was dissolved in approximately 350 mL of ethyl acetate at about 44° C. Approximately 175 mL of hexane was added with stirring until product began to precipitate.

A sealed vial containing the mixture was placed in a refrigerator at 4° C. overnight to crystallize. Recrystallization in ethyl acetate/hexane was repeated once more to give the final product, which was dried in vacuo for about 12 hours.

The identity of the sample as Ritonavir Form I was established by powder X-ray diffraction (distinguishing peaks at 3.3, 6.8, 8.4, and 21.6 2-theta) and purity by elemental analysis (Calcd. %—C, 61.66; H, 6.66; N, 11.66. Obsd. %—C, 61.74; H, 6.78; N, 11.41).

5.2. Example 2

Preparation of Ritonavir(III)

In order to prepare Ritonavir(III), 10 mg of Ritonavir Form I obtained in Example 1 above, 37.5 µL of formamide, and 12.5 µL of toluene (50 µL solvent total, containing 75% formamide) were deposited into a crimp-top 200 µL capacity glass vial. The vial was sealed with a crimp top and subsequently incubated at 70° C. until the Ritonavir solid dissolved. The vial was then cooled at a rate of approximately 5° C./minute to 5° C. The vial was incubated at 5° C. until crystals were observed. The crystals in the vial were removed from the supernatant by filtration, air dried, and characterized as described herein.

Ritonavir(III) was also prepared using the same process conditions from the following mixtures: 10 mg of Ritonavir Form I, 37.5 µL of formamide, and 12.5 µL of butyl acetate; and 10 mg of Ritonavir Form I, 37.5 µL of formamide, and 12.5 µL of acetone.

5.3. Example 3

Preparation of Ritonavir(IV)

50 mg of Ritonavir(III) obtained in Example 2 above was placed on filter paper in a Buchner funnel, which was fitted to a vacuum flask connected to an aspirator. With the vacuum on, 10 mL of deionized water was slowly poured over the solid Ritonavir(III). The resulting material on the filter was dried over vacuum for approximately 15 minutes, and characterized as described herein.

5.4. Example 4

Preparation of Ritonavir(V)

10 mg of Ritonavir Form I obtained in Example 1 above, 37.5 µL of butyl acetate, and 12.5 µL of acetonitrile (50 µL solvent total, containing 25% acetonitrile) were deposited into a crimp-top 200 µL capacity glass vial. The vial was sealed with a crimp top and subsequently incubated at 70° C. until the Ritonavir solid dissolved. The vial was then cooled at a rate of approximately 5° C./minute to 5° C. The vial was incubated at 5° C. until crystals were observed. The crystals in the vial were removed from the supernatant by filtration, and were subsequently air dried, and characterized as described herein.

Ritonavir(V) was also prepared using the same conditions from the following mixtures: 10 mg of Ritonavir Form I, 25 µL of isobutyl acetate, and 25 µL of acetonitrile; and 10 mg of Ritonavir Form I, 25 µL of isopropyl acetate, and 25 µL of acetonitrile.

5.5. Example 5

Characterization of Ritonavir Solid Forms

Each of the novel forms of Ritonavir was characterized by DSC, TGA, Raman spectroscopy, and powder X-ray diffraction spectroscopy. As discussed below, the data obtained using these methods make it clear that each of the forms is distinct from Forms I and II.

5.5.1. Instrumentation

DSC data were collected for each of the forms using a Q1000 Differential Scanning Calorimeter (TA Instruments, 109 Lukens Drive, New Castle, DE 19720), which uses as its control software Advantage for QW-Series, version 1.0.0.78, Thermal Advantage Release 2.0, © 2001 (TA instruments—Waters LLC). An aliquot of the sample was weighed into an aluminum sample pan (Pan part # 900786.091; lid part # 900779.901; TA Instruments, 109 Lukens Drive, New Castle, Del. 19720). The sample pan was sealed by press fitting the lid. The sample pan was loaded into the apparatus, which is equipped with an autosampler, and a thermogram was obtained by individually heating the sample at a rate of 10° C./min from $T_{min}$ (typically 20° C.) to $T_{max}$ (typically 300° C.) using an empty aluminum pan as a reference. Dry nitrogen was used as sample purge gas at a flow rate of 50 ml/min (compressed nitrogen, grade 4.8, BOC Gases, 575 Mountain Avenue, Murray Hill, N.J. 07974-2082). Thermal transitions were viewed and analyzed using the analysis software Universal Analysis. 2000 for Windows 95/95/2000/NT, version 3.1 E; Build 3.1.0.40, © 1991–2001 (TA instruments—Waters LLC), provided with the instrument.

TGA data were collected for each of the forms using a Q500 Thermogravimetric Analyzer (TA Instruments, 109 Lukens Drive, New Castle, Del. 19720), which uses as its control software Advantage for QW-Series, version 1.0.0.78, Thermal Advantage Release 2.0, © 2001 (TA instruments—Waters LLC). An aliquot of the sample was transferred into a platinum sample pan (Pan part # 952019.906; TA Instruments, 109 Lukens Drive, New Castle, Del. 19720). The pan was placed on the loading platform and was then automatically loaded in to the apparatus using the control software. Thermograms were typically obtained by individually heating the sample at 10° C./min from 25° C. to 300° C. under flowing dry nitrogen (compressed nitrogen, grade 4.8, BOC Gases, 575 Mountain Avenue, Murray Hill, N.J. 07974-2082), with a sample purge flow rate of 60 ml/min and a balance purge flow rate of 40 ml/min. Thermal transitions (weight changes) were viewed and analyzed using the analysis software Universal Analysis 2000 for Windows 95/95/2000/NT, version 3.1E; Build 3.1.0.40, © 1991–2001 (TA instruments—Waters LLC), provided with the instrument.

Raman data were collected for each of the novel forms of this invention, as well as for Forms I and II, using a Nicolet Almega™ Dispersive Raman system fitted with a 785 nm laser source and controlled by the Omnic for Almega software v. 5.2a. The sample was either left in the glass vial in which it was processed or an aliquot of the sample was transferred to a glass slide. The glass vial or slide was positioned in the sample chamber. The sample was manually brought into focus using the microscope portion of the apparatus with a 10× power objective (unless otherwise noted), thus directing the laser onto the surface of the sample. Spectra were collected in the 3250 to 105 cm$^{-1}$ range, using a 100 µm pin-hole aperture and sixteen, 2-second exposures. The resulting spectra were displayed using the control software.

Powder X-ray diffraction patterns were collected for each of the novel forms of this invention, as well as for Forms I and II. All X-ray powder diffraction patterns were obtained using the D/Max Rapid X-ray Diffractometer (D/Max Rapid, Rigaku/MSC, 9009 New Trails Drive, The Woodlands, Tex., USA 77381-5209), controlled by the RINT Rapid Control Software (Rigaku Rapid/XRD, version 1.0.0, © 1999 Rigaku Co.) and equipped with a copper source (Cu/K$_\alpha$=1.5406 Å), manual x-y stage, and 0.3 mm collimator. The sample was loaded into a 0.3 mm boron rich glass capillary tube (Charles Supper Company, 15 Tech Circle, Natick Mass. 01760-1024) by sectioning off an end of the tube and tapping the open end into a bed of the sample. The loaded capillary was mounted in a holder that was secured onto the x-y stage. A diffractogram was acquired under ambient conditions at 46 kV and 40 mA in transmission mode, while oscillating about the omega-axis from 0–5 degrees at 1 degree/s and spinning about the phi-axis at 2 degrees/s. The exposure time was 15 minutes unless otherwise specified. The diffractogram obtained (Debye ring diffraction on the image plate detector) was integrated over 2-theta from 2 to 60 degrees and chi (1 segment) from 0 to 360 degrees at a step size of 0.02 degrees using the cylint utility in the RINT Rapid Display software (version 1.18, Rigaku/MSC). The dark counts value was set to 8, normalization was set to average, and no omega, chi or phi offsets were used for the integration. The integrated diffraction patterns were analyzed using JADE XRD Pattern Processing software, versions 5.0 and 6.0 (© 1995–2002, Materials Data, Inc.).

5.5.2. Results

Using the DSC and TGA data obtained for Ritonavir Forms III, IV, and V, and published data for Forms I and II, the different thermal characteristics of each of the forms of Ritonavir were determined. These characteristics are provided below in Table 1:

TABLE 1

| Form | m.p. (° C.) | TGA % weight loss (up to 130° C.) | Crystal Habit |
|---|---|---|---|
| I | 122 | <0.3 | lath |
| II | 125 | <0.3 | needles |
| III | 80 ± 2 | 30—60 | needles |
| IV | 99 ± 2 | 4—9 | needles |
| V | 116 ± 2 | <0.3 | lath |

The data for Forms I and II were obtained from Chemburkar. The difference in the thermal properties of the various forms of Ritonavir is apparent from the conversion of Ritonavir (III) to Ritonavir(IV), which is shown by DSC in FIG. 17.

Raman spectra of each of the five forms of Ritonavir are shown in FIGS. 1, 3, 7, 11, and 15. Peaks distinctive of each form using a dispersive Near-IR laser-based Raman spectrometer are listed below in Table 2:

TABLE 2

| Form | Unique Raman Peaks (cm$^{-1}$) |
|---|---|
| I | 428.1, 821.3, 928.1, 966.3, 982.7, 1033.2, 1452.5, 1444.2, 1461.9, 1647.9 |
| II | 417.4, 443.4, 579.9, 954.1, 1029.1, 1662.0 |
| III | 691.13, 1393.29 |
| IV | 1404.73 |
| V | 814.6, 963.7 |

The distinct nature of each of the forms of Ritonavir is also evident from powder X-ray diffraction data. Graphical and tabular X-ray diffraction data for each of the three forms of the compound are provided in FIGS. 8, 12, and 16. Several peaks that are distinctive to each form are listed below in Table 3:

TABLE 3

| Form | Unique X-ray Diffraction Peaks (degrees 2-Theta) |
|---|---|
| III | 3.1, 6.8, 7.7, 8.3, 9.2, 10.5, 12.1, 13.1 |
| IV | 3.1, 6.1, 9.2, 12.1, 13.8 |
| V | 3.4, 6.4, 9.9, 12.7, 13.6, 15.3, 15.8, 17.5 |

The difference between the forms is even more apparent from FIG. 18, which provides a comparison of diffractograms obtained for each of the forms of Ritonavir. These data show that Ritonavir(III) and Ritonavir(IV) exhibit highly similar XRD patterns, which is consistent with a conserved structure that is solvated in one form (Ritonavir (III)) and partially (or essentially fully) desolvated in another form (Ritonavir(IV)).

5.5. Example 5

Conversion of Form V to Form I

Ritonavir(V) can transform into other forms of Ritonavir under certain conditions. For example, if Ritonavir(V) is prepared as above in Example 3, it was found to form a mixture of Forms V and I when left in the crystallization mixture for a prolonged period of time (hours to days). In a particular instance, Ritonavir(V) that was left in the crystallization mixture for approximately 16 hours at the nucleation temperature of 5° C. formed Ritonavir(I) as evidenced by X-ray diffraction (FIG. 19) and DSC (FIG. 20).

While the invention has been described with respect to the particular embodiments, it will be apparent to those skilled in the art that various changes and modifications may be made without departing from the spirit and scope of the invention as recited by the appended claims.

What is claimed is:

1. Ritonavir Form III characterized by a melting point from about 78° C. to about 82° C. and by a powder X-ray diffraction pattern containing peaks at 3.1, 6.8, 7.7, 8.3, 9.2, 10.5, 12.1, and 13.1 degrees 2-Theta.

2. The Form III of claim 1, wherein said Form III is further characterized by a Raman spectra with peaks at 691.1 and 1393.3 cm$^{-1}$.

3. Ritonavir Form IV characterized by a melting point from about 97° C. to about 101° C. and by a powder X-ray diffraction pattern containing peaks at 3.1, 6.1, 9.2, 12.1, and 13.8 degrees 2-Theta.

4. The Form IV of claim 3, wherein said Form IV is further characterized by a Raman spectra with a peak at 1404.7 cm$^{-1}$.

5. Ritonavir Form V characterized by a melting point from about 114° C. to about 118° C. and by a powder X-ray diffraction pattern containing peaks at 3.4, 6.4, 9.9, 12.7, 13.6, 15.3, 15.8, and 17.5 degrees 2-Theta.

6. The Form V of claim 5, wherein said Form V is further characterized by a Raman spectra with peaks at 814.6 and 963.7 cm$^{-1}$.

\* \* \* \* \*